United States Patent
Peterson et al.

(10) Patent No.: US 9,834,490 B1
(45) Date of Patent: Dec. 5, 2017

(54) SOLAR-ENRICHED BIOFUELS VIA LOOPED OXIDE CATALYSIS

(71) Applicant: Brown University, Providence, RI (US)

(72) Inventors: Andrew A. Peterson, Providence, RI (US); Cory M. Hargus, Providence, RI (US); Ronald Michalsky, Providence, RI (US)

(73) Assignee: Brown University, Providence, RI (US)

( * ) Notice: Subject to any disclaimer, the term of this patent is extended or adjusted under 35 U.S.C. 154(b) by 383 days.

(21) Appl. No.: 14/451,132

(22) Filed: Aug. 4, 2014

Related U.S. Application Data

(60) Provisional application No. 61/861,730, filed on Aug. 2, 2013.

(51) Int. Cl.
*C10G 3/00* (2006.01)
*C07C 1/22* (2006.01)

(52) U.S. Cl.
CPC ............ *C07C 1/22* (2013.01); *C07C 2523/06* (2013.01)

(58) Field of Classification Search
CPC ... C10G 3/40; C10G 3/00; C10G 3/42; C10G 3/64; C10G 3/50; C10G 3/45; C07C 1/00; C07C 1/20; C07C 1/22; C07C 1/24
USPC ......................................... 585/638, 639, 640
See application file for complete search history.

(56) References Cited

U.S. PATENT DOCUMENTS

| | | | |
|---|---|---|---|
| 4,443,326 A | 4/1984 | Field | |
| 4,721,694 A | 1/1988 | Buss et al. | |
| 5,559,068 A | 9/1996 | Chen et al. | |
| 7,977,517 B2 | 7/2011 | Cortright et al. | |
| 8,053,615 B2 | 11/2011 | Cortright et al. | |
| 8,217,211 B2 | 7/2012 | Agrawal et al. | |
| 8,287,610 B2 | 10/2012 | Weimer et al. | |
| 8,350,108 B2 | 1/2013 | Cortright et al. | |
| 8,541,637 B2 | 9/2013 | Babicki et al. | |
| 2010/0043278 A1 | 2/2010 | Brevoord et al. | |
| 2012/0029252 A1 | 2/2012 | Lissianski et al. | |
| 2012/0036764 A1 | 2/2012 | Babe et al. | |
| 2012/0203043 A1 | 8/2012 | Wheeler et al. | |
| 2012/0222349 A1 | 9/2012 | Truitt et al. | |

(Continued)

FOREIGN PATENT DOCUMENTS

| | | |
|---|---|---|
| WO | WO 2012035410 | 3/2012 |
| WO | WO 2012087505 | 6/2012 |

(Continued)

OTHER PUBLICATIONS

Peterson et al. "Thermochemical biofuel production in hydrothermal media: a review of sub- and supercritical water technologies" *Energy Environ. Sci.* [Online] 2008, 1, pp. 32-65.

(Continued)

*Primary Examiner* — Sharon Pregler
(74) *Attorney, Agent, or Firm* — Adler Pollock $ Sheehan P.C.; Daniel J. Holmander

(57) ABSTRACT

The invention is an integrated thermochemical process, also known as a looped-oxide catalysis, for providing an upgraded biofuel composition from a biomass-derived feedstock. First, the feedstock is deoxygenated through reaction with a low-valence metal oxide or zero-valent metal to yield a deoxygenated biofuel composition and a high-valence metal oxide. Second, the low-valence metal oxide is regenerated by reducing the high-valence metal oxide using solar thermal energy.

20 Claims, 13 Drawing Sheets

(56) References Cited

U.S. PATENT DOCUMENTS

2013/0245330 A1     9/2013   He et al.
2015/0099908 A1*   4/2015   Xiao et al. ................ C10L 1/02
                                                                                         585/240

FOREIGN PATENT DOCUMENTS

WO     WO 2013103768     7/2013
WO     WO 2013134220     9/2013

OTHER PUBLICATIONS

Prasomsri et al. "Effective hydroeoxygenation of biomass-derived oxygenates into unsaturated hydrocarbons by MoO3 using low $H_2$ pressures" *Energy Environ. Sci.* [Online] 2013, 6, pp. 1732-1738.

Santillan-Jimenez et al. "Catalytic deoxygenation of fatty acids and their derivatives to hydrocarbon fuels via decarboxylation/decarbonylation" *J. Chem. Technol. Biot.* [Online] 2012, 87, pp. 1041-1050.

Zinoviev et al. "Next-generation biofuels: Survey of emerging technologies and sustainability issues" *ChemSusChem* [Online] 2010, 3, pp. 1106-1133.

* cited by examiner

SOLAR-ENRICHED BIOFUELS VIA LOOPED OXIDE CATALYSIS

CROSS REFERENCE TO RELATED APPLICATION

This non-provisional patent application is related to and claims priority from earlier filed U.S. Provisional Patent Appl. No. 61/861,730 filed Aug. 2, 2013, incorporated by reference herein.

BACKGROUND OF THE INVENTION

The invention is an integrated thermochemical process, also known as a looped-oxide catalysis, for providing an upgraded biofuel composition from a biomass-derived feedstock. First, the feedstock is deoxygenated through reaction with a low-valence metal oxide or zero-valent metal to yield a deoxygenated biofuel composition and a high-valence metal oxide. Second, the low-valence metal oxide is regenerated by reducing the high-valence metal oxide using solar thermal energy.

Instabilities in the price of petroleum and the impact of fossil fuel combustion on global climate change demand that a clean and renewable source of transportation fuels be developed; particularly one that will not require major changes to the existing infrastructure of fuel consumption. Given their high energy density it is likely that liquid hydrocarbon fuels will play a dominant role in the foreseeable future of the ever-expanding transportation industry.

While petroleum-derived fuels constitute the bulk of transportation fuels currently in use, there are many available fuel upgrade paths for converting cellulosic biomass into value-added fuels including Fischer-Tropsch synthesis and hydrodeoxygenation (HDO) or zeolite upgrading of bio-oils. In general, cellulosic biomass feedstocks represent a good starting material for liquid fuel production but such feedstocks typically have high oxygen contents and, consequently, low combustion energy densities. At the same time, alternative energy sources such as solar, wind and geothermal power are gaining traction in the energy industry but are generally limited to supplying electrical energy to the grid. Solar energy is the largest exploitable renewable resource by far; the energy available from terrestrial insolation far exceeds the needs of human consumption.

Bio-oils obtained from the thermal processing of cellulosic biomass represent a promising feedstock for the production of renewable fuels; however, without deep upgrading their direct use as a fuel is extremely limited. Therefore the development of hydroprocessing technologies for the upgrading of bio-oils to utilizable transportation fuels is of great importance. Hydroprocessing involves the addition of hydrogen gas into a low-grade liquid fuel in the presence of a solid catalyst. The goal of hydroprocessing is to improve fuel quality by removal of heteroatoms, resulting in higher energy content, volatility and thermal stability and lower viscosity and molecular weight. Because oxygen is the predominant heteroatom in bio-oils, studies on bio-oil hydroprocessing tend to focus on hydrodeoxygenation (HDO) as the primary reaction pathway.

There are two principal avenues leading from raw cellulosic biomass to bio-oils: fast pyrolysis and liquefaction. Fast pyrolysis is the rapid thermal decomposition of biomass in the absence of oxygen. Liquefaction is the decomposition of biomass in hydrothermal media. Due to their high oxygen content both fast pyrolysis and liquefaction oils are generally unusable without deep upgrading.

It would therefore be desirable to provide a more efficient and optimized process for providing an upgraded biofuel composition from a feedstock.

BRIEF SUMMARY OF THE INVENTION

The invention is an integrated thermochemical process, also known as a looped-oxide catalysis, for providing an upgraded biofuel composition from a biomass-derived feedstock. First, the feedstock is deoxygenated through reaction with a low-valence metal oxide or zero-valent metal to yield a deoxygenated biofuel composition and a high-valence metal oxide. Second, the low-valence metal oxide is regenerated by reducing the high-valence metal oxide using solar thermal energy.

In one embodiment, the deoxygenating is conducted at a pressure of 1-50 bar, preferably at a pressure of 1-10 bar, and more preferably at ambient total pressure.

In one embodiment, a hydrodeoxygenation process is conducted using $H_2$ generated through the in situ reaction of the low-valence or zero-valent metal oxide with water inside a reactor.

In one embodiment, the feedstock is a low-energy bioliquid. In another embodiment, the feedstock is bio-oil derived from thermal processing of lignocellulosic biomass.

In one embodiment, the zero-valent metal, the low-valence metal oxide, or the high-valence metal oxide comprises a metal that is selected from the group consisting of: Fe, Zn, Ge, Mo, Cd, Sn, Ce, W, or mixtures, combinations, or variations thereof. In another embodiment, the low-valence metal oxide or zero-valent metal is selected from the group consisting of: FeO, Zn, Cd, SnO, $Ce_2O_3$, or mixtures, combinations, or variations thereof. In another embodiment, the high-valence metal oxide is selected from the group consisting of: $Fe_3O_4$, ZnO, CdO, SnO2, CeO2 or mixtures, combinations, or variations thereof. Of course, it is contemplated that other low-valence metal oxides, zero-valent metals, or high-valence metal oxides, and other mixtures, combinations, and variations thereof, may be used in accordance with parameters discussed herein.

In one embodiment, the zero-valent metal, said low-valence metal oxide, or said high-valence metal oxide acts as a catalyst in determining selectivity towards targeted deoxygenation products. In one embodiment, the zero-valent metal or said low-valence metal oxide acts as a bulk reducing agent and oxygen conductor in removing oxygen heteroatoms from the feedstock.

In one embodiment, the regenerating the low-valence metal oxide is performed within a solar thermal reactor.

In one embodiment, the deoxygenating of the feedstock occurs at a temperature between 300-700 K, preferably to a temperature between 400-600 K, and more preferably to a temperature of 500 K. Of course, these temperatures are preferred ranges which maybe subject to change depending upon the requirements of the reaction.

In one embodiment, the regenerating of the low-valence metal oxide occurs at a dissociation temperature of the high-valence metal oxide.

In one embodiment, the regenerating of the low-valence metal oxide occurs at temperature between 1000-2000 K, preferably to a temperature between 1200-1800 K, more preferably to a temperature between 1400-1600, and even more preferably at 1500 K. Of course, these temperatures are preferred ranges which maybe subject to change depending upon the requirements of the reaction.

In one embodiment, regenerating a low-valence metal oxide is accomplished in a solar electrothermal reactor where the metal oxide is dissolved in a molten electrolyte.

BRIEF DESCRIPTION OF THE DRAWINGS

The novel features which are characteristic of the present invention are set forth in the appended claims. However, the method and system of the present invention together with further embodiments and attendant advantages, will be best understood by reference to the following detailed description taken in connection with the accompanying drawings in which:

DETAILED DESCRIPTION OF THE PREFERRED EMBODIMENTS

Referring generally to FIGS. 1-13, this invention relates in general to an integrated thermochemical process, also known as a looped-oxide catalysis, for providing an upgraded biofuel composition from a biomass-derived feedstock. First, the feedstock is deoxygenated through reaction with a low-valence metal oxide or zero-valent metal to yield a deoxygenated biofuel composition and a high-valence metal oxide. Second, the low-valence metal oxide is regenerated by reducing the high-valence metal oxide using solar thermal energy.

Figure 1:
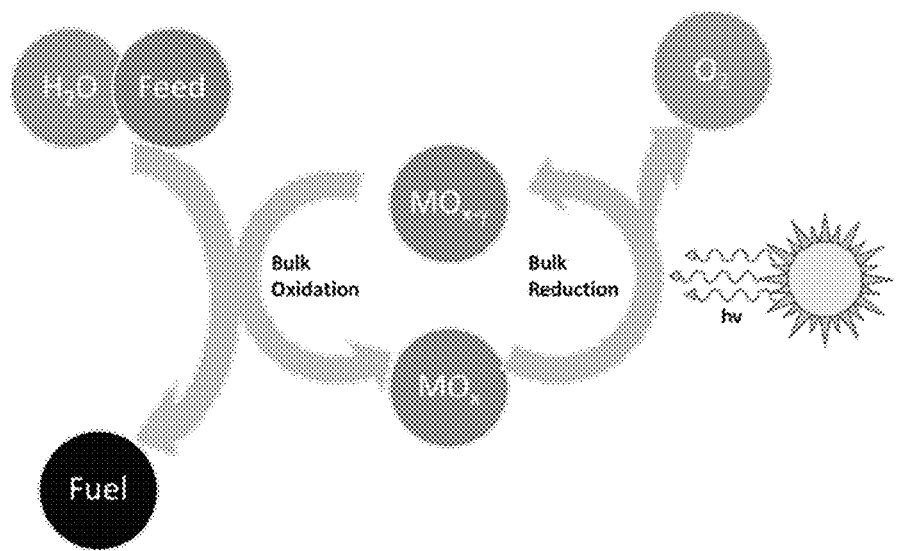
FIG. 1 is a schematic view for in situ hydrodeoxygenation (HDO) of bioliquid feeds utilizing a two-step thermochemical cycle (TC).

Referring to FIG. 1, a schematic view for in situ hydrodeoxygenation (HDO) of bioliquid feeds is provided utilizing a two-step thermochemical cycle (TC). Despite attractive yields, HDO upgrading is limited by the requirement for very high hydrogen partial pressure which is not required for the two-step thermochemical cycle. This requirement is circumvented in the proposed alternative upgrade pathway, termed "looped-oxide catalysis", wherein a bio-oil feedstock is deoxygenated over a bulk-reduced metal oxide catalyst as part of a two-step solar thermochemical cycle.

One half of the TC, in which the metal oxide is reduced to its metal or to a low-valence metal oxide, is given by reaction (7) below:

$$MO_x \rightarrow MO_{x-\delta} + \frac{\delta}{2} O_2 \qquad (7)$$

The other half, in which the bioliquid feedstock is upgraded via HDO during the re-oxidation of the reduced oxide, is a combination of reaction (8):

$$MO_{x-\delta} + \delta H_2O \rightarrow MO_x + \delta H_2. \qquad (8)$$

with reactions (3) through (6).

$$C_6H_9O_4 + 7H_2 \rightarrow C_6H_{14} + 4H_2O \qquad (3)$$

$$RCOOH \rightarrow RH + CO_2 \qquad (4)$$

$$RCOOH + H_2 \rightarrow RH + CO + H_2O \qquad (5)$$

$$RCOOH + 3H_2 \rightarrow RCH_3 + 2H_2O \qquad (6)$$

This pathway represents the re-oxidation of the reduced, splitting water to form $H_2$ which goes on to react with a feed molecule in an HDO reaction. For the purpose of the analysis, it will be assumed that gas-phase $H_2$ is generated during the re-oxidation step before it is consumed in the HDO process. In reality, surface HDO reactions occurring at coordinatively unsaturated exposed metal cations and hydroxyl groups may occur before the formation of gas-phase $H_2$. Consideration of the specific possibilities relating to reaction mechanism and the use of bulk-reduced metal oxides as catalyst supports will be given below. Whether the metal oxide serves as the catalyst or as a support, the net effect of the looped-oxide catalysis is the transfer of solar energy obtained during thermal reduction into the bioliquid feedstock in an HDO-like upgrading reaction.

In choosing candidate metal oxide redox pairs for looped-oxide catalysis, there are three criteria which any acceptable cycle must meet:

1. The thermodynamics of the redox cycle must allow for the generation of gas-phase $H_2$ at the selected temperature while minimizing the energetic cost of the reduction step; in other words the ΔG of reaction (8) must approach zero while the ΔG of reaction (7) is minimized;

2. Each reaction step must proceed at an acceptable rate, particularly oxygen anion interstitial and vacancy diffusion through the oxide front; and 3. The metal oxide formed during the bulk oxidation step must function as either a catalyst or a catalyst support for HDO-type reactions. In addition to these three constraints, consideration should be given to the cost and nature of any separation steps and to the weight, toxicity and the global cost and availability of the candidate species.

Figure 2:
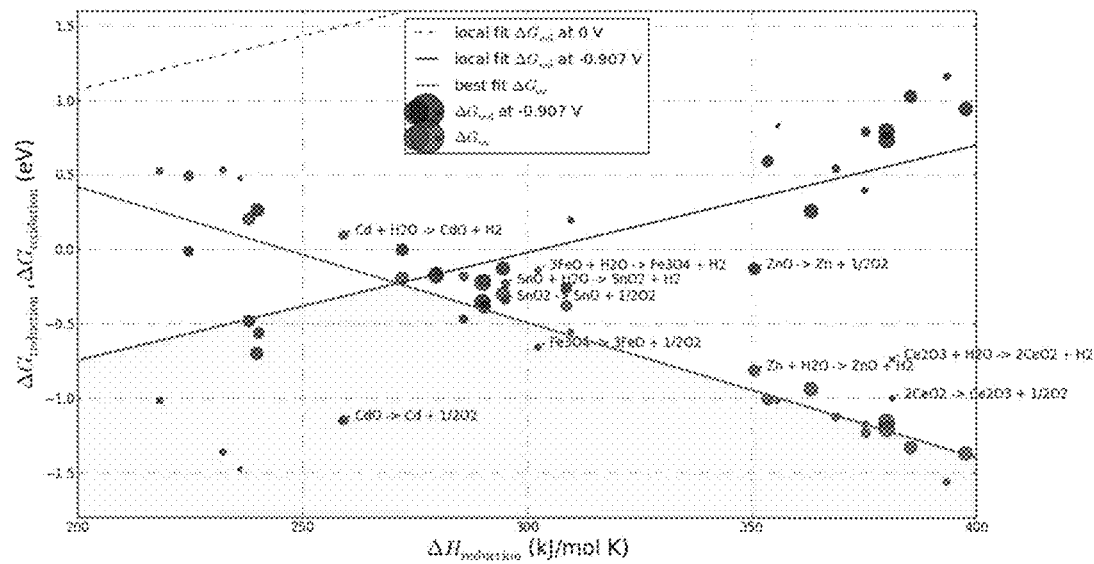
FIG. 2 is a graph of a pseudo-Volcano plot for metal oxide thermochemical cycles (TCs) with the five candidate cycles annotated.

Referring to FIG. 2, a graph showing a Pseudo-Volcano plot for metal oxide TCs with the five candidate cycles annotated is provided. Red and blue points represent the ΔG of oxidation at 500 K (in KJ/mole $H_2$) and ΔG of reduction at 1500 K and −0.907 V (KJ/½ mole $O_2$), respectively, plotted against ΔH of reduction at 500K, which is used as a measure of the reduced oxide's oxygen binding strength. The dashed line is a regression fit for the ΔG of reduction with no added voltage. Red and blue lines are regression fits for the plotted data points. The weight of each data point corresponds to the mass of oxide per mole of $H_2$ generated in reaction (8).

Because the looped-oxide catalysis seeks to bypass the need for an exogenous source of $H_2$, effective thermochemical performance for the in situ generation of $H_2$ is considered the primary criterion in candidate cycle selection. In developing an effective metric for optimizing thermochemical performance we turn to an analogue in catalysis: the Sabatier Principle states that the interaction between a catalyst and its substrate should be neither too strong (the catalyst surface sites will be blocked) nor too weak (the substrate will not bind and no reaction will occur). This is often invoked in catalysis science to create a "volcano plot" where the activities of different catalysts are plotted against substrate binding energy or any other parameter pertaining to the catalyst surface's ability to form bonds with substrates. The Sabatier Principle may also be applied to looped-oxide catalysis: the reduced oxide should bind oxygen tightly enough that it is able to split water or abstract oxygen atoms from the oxygenate species, but not so tightly that the formed oxide requires excess energy to reduce. Therefore, there has been identified eighty potential looped-oxide cycles and have constructed a pseudo-volcano plot in which the Gibbs free energy of reduction and the Gibbs free energy of oxidation for each oxide redox pair are plotted against the corresponding enthalpy of reduction, which is used as a metric of oxygen binding strength. FIG. 2 is a detail of the volcano "peak", where the most interesting candidate metal oxide redox cycles lie. It is assumed that the oxidation step takes place at 500 K and that the reduction step takes place at 1500 K and at a reduction potential of −0.907 V. This is the potential necessary to make the reduction of FeO to Fe exergonic. −0.907 V was chosen as a benchmark reduction potential because the FeO/Fe cycle with the lowest ΔH of reduction which will split water at 500 K. It is also assumed that all oxides step linearly through oxidation states during redox reactions and that discrete oxidation states exist for all oxides according to the format used in the source of thermochemical data. On the basis of thermochemical performance, as illustrated in FIG. 2, five candidate cycles were identified: FeO/Fe3O4, Zn/ZnO, Cd/CdO, SnO/SnO2 and Ce2O3/CeO2. These cycles were also selected based on their diffusion kinetics and their performance as HDO catalysts, as will be discussed in detail in the next section.

The non-thermodynamic parameters of the five candidate cycles identified in the previous section are discussed in detail herein. Because the re-oxidation of the bulk-reduced oxide is most likely the rate-limiting step in solar thermochemical production of hydrogen, this parameter has been given the greatest weight and will be discussed in detail.

$FeO/Fe_3O_4$

The use of metal oxide thermochemical cycling for hydrogen production was first proposed for the redox pair $FeO/Fe_3O_4$. Beyond its desirable thermodynamics, the principal advantages of iron oxide systems are cost and global availability of materials and the solid phase of both reactants and products (in contrast to Zn/ZnO and Cd/CdO cycles, where the gaseous phase of the metal at reduction temperatures necessitates a quenching step). One other feature of iron oxide systems is the potential for partial substitution in $FeO/Fe_3O_4$ by other metal oxides $MO/M_3O_4$ to achieve more desirable thermochemical, kinetic and material properties in the formed ferrite material. Ferrites such as $Ni_{0.5}Mn_{0.5}Fe_2O_4$ and $CuFe_2O_4$[4] have been studied in thermochemical cycling applications both in the partially-substituted spinel crystal phase and in ferrites synthesized through atomic layer deposition (ALD) of alternating layers of, e.g., $Fe_2O_3$ and CoO to achieve a bulk layered cobalt ferrite, $CoFe_2O_4$. Iron oxide cycles are, however, generally limited by the low rate of diffusion of oxygen into the bulk of the metal. For example, conversion of FeO to $Fe_3O_4$ in a hydrolysis reaction at 400° C. and 1 bar was found to be only 32% after 120 minutes. Additionally, to avoid recombination of FeO with oxygen upon reduction the reduction product must be quenched. Reduction and quenching to non-stoichiometric and nearly-stoichiometric wüstite is often desirable as the re-oxidation of these phases by water is much more rapid than that of stoichiometric FeO due to the high presence of bulk defects. Although $Fe_3O_4$ is not a traditional catalyst or support for hydroprocessing, it has been proposed as an HDO catalyst and behaves as a bifunctional catalyst in hydrogenation reactions. For example iron oxide demonstrated high activity and selectivity in the reaction of acetic acid to acetaldehyde when iron is present in both its oxide and metallic phases (necessitating a reactor hydrogen/acid ratio of >4).

Zn/ZnO

Another promising cycle for bioliquid upgrading through thermochemical cycling is Zn/ZnO. In addition to desirable oxidation/reduction thermodynamics, Zn/ZnO cycles demonstrate good exergy efficiency due to the relatively low heat capacity of ZnO. Perhaps the greatest limitation in Zn/ZnO TCs is the low rate of diffusion of oxygen anion interstitials and vacancies through ZnO. Upon oxidation, zinc particles have been observed to form a passivating layer of ZnO which prevents complete oxidation of the interior. To achieve oxidation yields of greater than 50%, Zn nanoparticles (diameter 70-100 nm) must be synthesized. Furthermore, because the metal product of the high-temperature reduction will exist in the gas phase, difficult quenching steps must be implemented in any Zn/ZnO TC to achieve good zinc metal recovery and avoid recombination with oxygen. On the other hand, regulation of quenching parameters following the reduction step allows for good control over material properties including particle size of the zinc metal. Reduction of ZnO in a thermal electrolytic cell at above the boiling point of Zn results in the evolution of gaseous zinc metal at the cathode and oxygen at the anode—a simple separation step that allows for greater flexibility in the zinc metal quenching conditions with zero recombination of products upon cooling. Reduction of ZnO by "quasi-electrolysis" has also been suggested, wherein a supersaturated solution of ZnO is heated in an electrolytic cell to a temperature at which reduction is exergonic but maintained at high-pressure to suppress spontaneous dissociation. Low-voltage electrolysis of the solution then evolves gaseous Zn and $O_2$ at separate electrodes and the electrical energy supplied simply becomes the energy of unmixing of gaseous Zn and $O_2$, about 19 kJ.

Cd/CdO

As with zinc oxide, the Cd/CdO TC also requires a quenching step after reduction. The primary difference is that Cd is quenched as a molten liquid, whereas Zn is quenched as a solid. Although recombination with oxygen during the quenching process may lead to a loss in reduced metal recovery, as before with the zinc oxide cycle an electrolytic set-up may be utilized to achieve separation. It may be possible to bypass diffusion limitations inherent to other metal oxide TCs by carrying out the oxidation of cadmium in its molten liquid state, however for a bioliquid upgrading application this may perpetuate the presence of trace cadmium in the upgraded fuel product. The use of cadmium is severely limited by its toxicity, which also dictates the role of process byproducts. Depending on regional legislation, non-toxic waste mineral ash from biofuel upgrading may be sold commercially as fertilizer, so the use of non-toxic materials will always be preferable. Cadmium oxide has not been investigated as a potential catalyst for bioliquid feedstock upgrading; research is limited to the use of CdO as a Lewis-acid catalyst for the hydrolysis, esterification and transesterification of triglycerides and fatty acids in bio-diesel production.

$SnO/SnO_2$

SnO is metastable at temperatures <600K and will disproportionate into Sn and $SnO_2$. Therefore, evaluation of this TC must take into consideration the presence of disproportionation products along with SnO. As with the non-stoichiometric wüstite phases in the iron oxide cycle, fast oxidation kinetics have been observed for the hydrolysis of SnO with no formation of a passivating oxide layer. However, the kinetics of a mixture of Sn and $SnO_2$ have been demonstrated to be slower with nanoparticles (50-100 nm) requiring an estimated one hour of reaction time to achieve over 70% conversion; therefore it is preferable to suppress disproportionation as much as possible. For this reason, the analysis here is focused on the formation of SnO as the reduction product. HDO over a $SnO_2$ catalyst has also been suggested due to its surface reducibility.

$Ce_2O_3/CeO_2$

The final cycle, $Ce_2O_3/CeO_2$, is often discussed in terms of oxygen vacancies, where a redox cycle has the form $CeO_2/CeO_{2-\delta}$. This cycle has demonstrated high rates of oxidation reaction kinetics with 100% conversion of mm-sized $Ce_2O_3$ particles to $CeO_2$ observed in less than five minutes at 600° C.; this is very fast compared to zinc and ferrite systems. The ceria cycle also has the advantage that the reduction product, $Ce_2O_3$ is stable in ambient air and will not re-oxidize, allowing for easier storage and transportation. However this redox pair is notably limited by mass transport cost; the reduction product, $Ce_2O_3$ has a molecular weight of 328.24 g/mole.

To evaluate the performance of the five candidate looped-oxide catalytic cycles identified in the previous section in a bioliquid feedstock upgrading process, a thermodynamic equilibrium model is developed with varying levels of constraint on product formation. This equilibrium model seeks to characterize the HDO half of the proposed thermochemical cycle (TC), in which the reduced oxide is re-oxidized and the organic feedstock is upgraded in an HDO reaction pathway. This is followed by an efficiency treatment of the other half of the proposed TC—the high-temperature bulk reduction of the oxide in a solar furnace. Finally, an exergy analysis is performed on the process as a whole to identify areas of inefficiency and to compare between theoretical performances of the candidate oxide cycles. For this analysis we have adopted acetaldehyde as a model feedstock compound; it is a common component of bio-oil and is the simplest oxygenate containing both a C—C and a C—O bond.

The equilibrium behavior of each of the candidate reduced oxides in the feedstock upgrading process was assessed using a thermodynamic equilibrium model. Although only descriptive of systems at long timescales, such an equilibrium model represents a useful engineering tool for demonstrating the effect of process conditions and reactant selection on the species composition of the system. The NASA CEA algorithm was employed using nine-term polynomial data from the NASA database augmented with tabular data from the Barin Thermochemical Tables which was converted to polynomial form and formatted according to the NASA PAC program. The NASA CEA algorithm, which works by minimizing the Gibbs energy of the chemical system subject to elemental conservation, is useful for describing systems in which specifying individual stoichiometric reactions can be cumbersome because of the many species which may be formed.

Equilibrium models were developed for three separate scenarios corresponding to varying levels of constraint with respect to the number of species considered, as summarized in Table 3.1.

TABLE 3.1

Chemical species considered by thermodynamic equilibrium model

| Scenario | Phase | Category | Species |
|---|---|---|---|
| All | Gas | Gaseous metal and oxide species | Cd, Zn, Sn, SnO, SnO2, Fe, FeO |
|  | Solid | Condensed metal and oxide species | Cd(s), Cd(l), Zn(s), Zn(l), Sn(s), Sn(l), SnO(s), SnO(l), SnO2(s), SnO2(l), Fe(a,s), Fe(c,s), Fe(d,s), Fe(l), FeO(s), FeO(l), Fe3O4(s), Fe3O4(l), Fe2O3(s), Ce2O3(s), CeO2(s) |
| Un-constrained | Gas | Inorganic carbon compounds | C(g), CO, CO2 |
|  |  | Hydrogen and oxygen compounds | H2, H2O, H, HO2, H2O2, O, O2, O3 |
|  |  | Organics compounds | CH, CH2, CH3, CH4, CH2OH, CH3O, CH3OH, CH3OOH, COOH, C2H, C2H2 (acetylene) C2H2 (vinylidene), CH2CO (ketene), O(CH)2O, HO(CO)2OH, C2H3 (vinyl), CH3CO (acetyl), C2H4, C2H4O (ethylen-o), CH3COOH, CH3CHO (acetaldehyde), OHCH2COOH, C2H5, C2H6, Higher hydrocarbons and organics |
|  | Solid | Carbon | C(s) |
| Constrained | Gas | Inorganic carbon compounds | CO, CO2 |

TABLE 3.1-continued

Chemical species considered by thermodynamic equilibrium model

| Scenario | Phase | Category | Species |
|---|---|---|---|
| | | Hydrogen and oxygen compounds | H2, H2O, O2 |
| | | Organics compounds | CH3CHO (acetaldehyde), C2H4 |
| Hyper-Constrained | Gas | Hydrogen and oxygen compounds | H2O, O2 |
| | | Organics compounds | CH3CHO (acetaldehyde), C2H4 |

In each scenario, two runs were performed; one with equimolar amounts of acetaldehyde and water and the other with equimolar amounts of acetaldehyde, water and the candidate reduced oxide. All equilibrium calculations were carried out at 1 bar of pressure and for temperatures between 400 and 1400 K.

Figure 3:
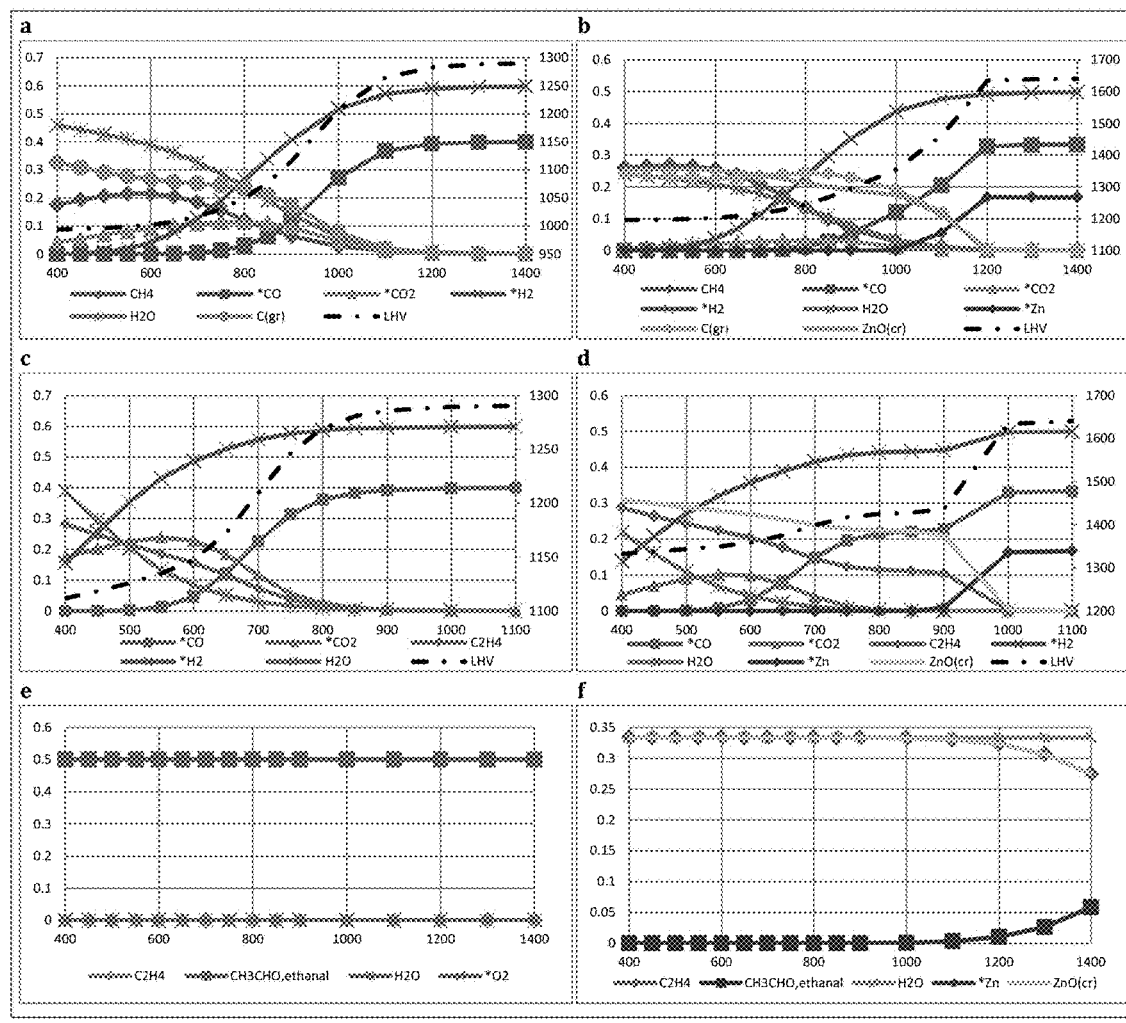
FIG. 3 is a graph of equilibrium composition plots for equimolar reaction of acetaldehyde and water (a,c,e) and equimolar zinc, acetaldehyde and water at 1 bar of pressure.
Figure 4:
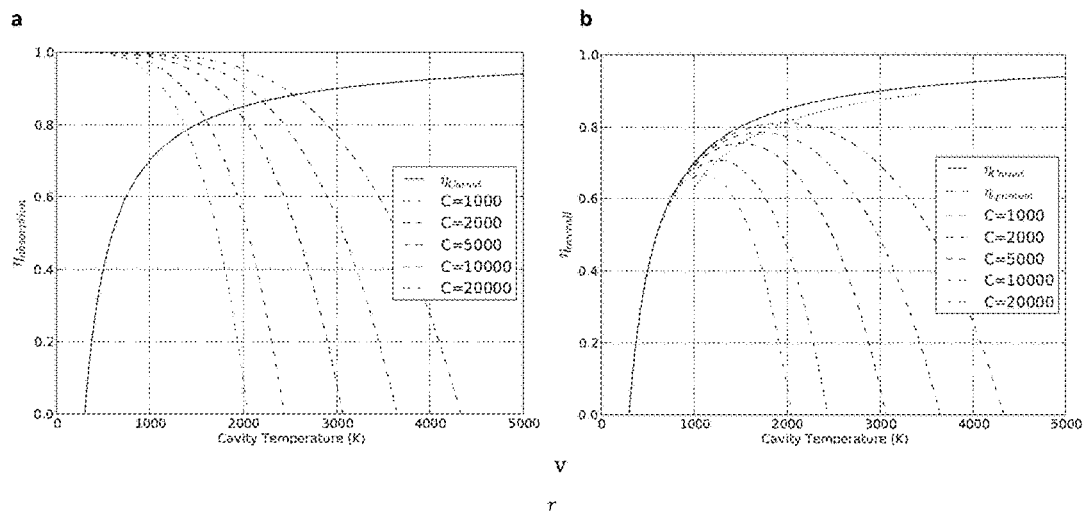
FIG. 4a is a graph of solar absorption efficiency, η_absorption, versus of temperature for select concentration rations.
FIG. 4b is a graph of overall efficiency of a solar furnace, η_overall, for select concentration ratios and optimum efficiency, ηoptimum, as functions of temperature.

Resulting data for acetaldehyde upgrading in the presence of metallic zinc is presented in FIG. 3 and is representative of the trend observed for each of the candidate reduced oxides. In the first scenario the equilibrium was unconstrained, allowing for the formation of any chemical species in the NASA database so long as an elemental balance with the input species was satisfied. In the absence of zinc (FIG. 3.1a), the reaction of acetaldehyde and water favors the production of CO and $H_2$ (syngas) at higher temperatures (>1200 K) via the water gas shift reaction. At lower temperatures (400-700 K), the formation of methane, graphite, water and $CO_2$ is favored. The addition of zinc (FIG. 3.1b) shifts the equilibrium towards an increased formation of methane and a decreased formation of graphite, water and $CO_2$ at lower temperatures (<1000 K) where the zinc is completely oxidized. At equilibrium, graphite accounts for 51% of the total carbon atoms in the absence of zinc and 45% of the total carbon atoms with zinc present. Graphite formation and deposition on the surface of HDO catalysts, as indicated in this equilibrium model, represents a considerable hurdle for catalyst designers. In commercial HDO of both biomass and fossil-fuel feeds, catalyst deactivation by carbon deposition has been demonstrated to be the main path of catalyst deactivation, and generally occurs by polymerization or polycondensation of feed molecules on the catalyst surface. Incorporating HDO into a solar TC, could circumvent the problem of catalyst coking by removal of surface carbons from the oxide surface upon each iteration of the TC during the high-temperature reduction step.

Referring to FIG. 3, a graph is provided for equilibrium composition plots for equimolar reaction of acetaldehyde and water (a,c,e) and equimolar zinc, acetaldehyde and water at 1 bar of pressure. In each figure, the x-axis represents temperature in Kelvin, while the primary y-axis (on the left) gives the mole fraction for each species and the secondary y-axis (on the right of a, b, c and d) gives the lower heating value of the species distribution in kJ per mole of reactants. a and b correspond to the unconstrained scenario, c and d to the constrained scenario, e and f to the hyper-constrained scenario.

In the second (constrained) scenario (FIG. 3 c, d) the equilibrium is confined to promote the formation of $C_2H_4$ as the only hydrocarbon product and to prevent the formation of graphite. Again, the addition of metallic zinc shifts equilibrium towards the formation of the hydrocarbon product, ethylene. The formation of ethylene (along with ethane, ethanol, and other products) from a pure acetaldehyde feed during upgrading over NiMo carbide has been experimentally observed, and a proposed mechanism for the deoxygenation of acetaldehyde to ethylene over $MoO_3$ has been modeled using density functional theory calculations. In the third (hyper-constrained) scenario (FIG. 3 e, f) the number of possible species is further restricted, essentially allowing only the stoichiometric deoxygenation of acetaldehyde along with the resultant oxidation of the bulk-reduced catalyst. This scenario corresponds to an ideal bulk-reduced oxide catalyst; one that accepts oxygen during the deoxygenation of acetaldehyde without activity towards the formation of graphite, excess $H_2$, or other unwanted side reactions. For the hyper-constrained case, all of the five candidate reduced oxides demonstrated 100% conversion of acetaldehyde to ethylene at 500 K and 1 bar with the exception of Cd, which showed 99.1% conversion.

The starting point for analyzing the efficiency of any TC is the Carnot efficiency, which describes the maximum theoretical efficiency of a heat engine operating between a heat source at temperature $T_h$ and a heat sink at temperature $T_c$. (For a simple derivation of the Carnot efficiency model as it is applied to TCs, see Ewan and Allen.)

$$\eta_{carnot} = 1 - \frac{T_c}{T_h} \quad (11)$$

$T_c$ is generally taken to be 298 K while $T_h$ may vary according to the conditions of the solar cavity. The Carnot efficiency model may be further refined for the case of a TC operated within a solar cavity, where some of the solar flux into the cavity of the furnace is lost to re-radiation, according to the Stefan-Boltzmann Law. Assuming perfect optics, perfect insulation and absorptivity and emissivity approaching unity, the absorption efficiency of a black body cavity is:

$$\eta_{absorption} = \frac{IC - \sigma T_h^4}{IC} \quad (12)$$

Here C denotes the "concentration ratio", which is a measure of solar flux intensity (e.g. in units of suns) after amplification through the use of mirrors or condensing lenses. Here, I represents the normal beam intensity of sunlight, taken to be 1 kW m$^{-2}$, and σ is the Stefan-Boltzmann constant. The maximum overall efficiency of a TC operated within a solar cavity is given by the product of the two efficiencies:

$$\eta_{overall} = \eta_{carnot} \times \eta_{absorption} \quad (13)$$

Referring to FIG. 4a, a graph is provided showing a solar absorption efficiency, $\eta_{absorption}$, versus of temperature for select concentration ratios. Referring to FIG. 4b, a graph is provided showing overall efficiency of a solar furnace, $\eta_{overall}$, for select concentration ratios and optimum efficiency, $\eta_{optimum}$, as functions of temperature.

Finally, by differentiating $\eta_{overall}$ with respect to $T_h$, setting the resulting expression equal to zero and solving for C, we may determine the optimum concentration ratio corresponding to any given solar cavity temperature:

$$C_{opt} = \frac{\sigma T_h^4(4T_h - 3T_c)}{T_c I} \quad (14)$$

FIGS. 4a and 4b give the absorption efficiency and overall efficiency, respectively, of a solar cavity as a function of temperature. In each, the efficiencies are plotted against the Carnot efficiency, and FIG. 4b also plots the efficiency of a solar cavity operating at $C_{opt}$, denoted $\eta_{optimum}$, as a function of the cavity temperature. As the cavity temperature, $T_h$, increases, $\eta_{optimum}$ approaches the Carnot efficiency. On each plot, the intersection of the efficiency curve with the x-axis represents the stagnation temperature for a solar cavity operating at a given concentration ratio. For the purposes of the exergy analysis in the following section, a cavity temperature of 1500 K was assumed for all cycles; this $T_h$ value corresponds to a $C_{opt}$ of 4920. As a reference for the reader, the three most common solar optical configurations for solar concentration are "trough", "tower", and "dish" systems, corresponding to typical concentration ratios, respectively, of 30-100, 500-5000 and 1000-10,000[85].

While the Carnot efficiency provides a useful benchmark for the theoretical upper bound on efficiency of the oxide reduction step, to evaluate the proposed process in its entirety for the five candidate oxides identified above for a more elaborate approach was employed. Herein we provide an exergy analysis for the performance of each candidate oxide in a black-box model of the proposed solar TC for the deoxygenation of acetaldehyde to ethylene.

Figure 5:
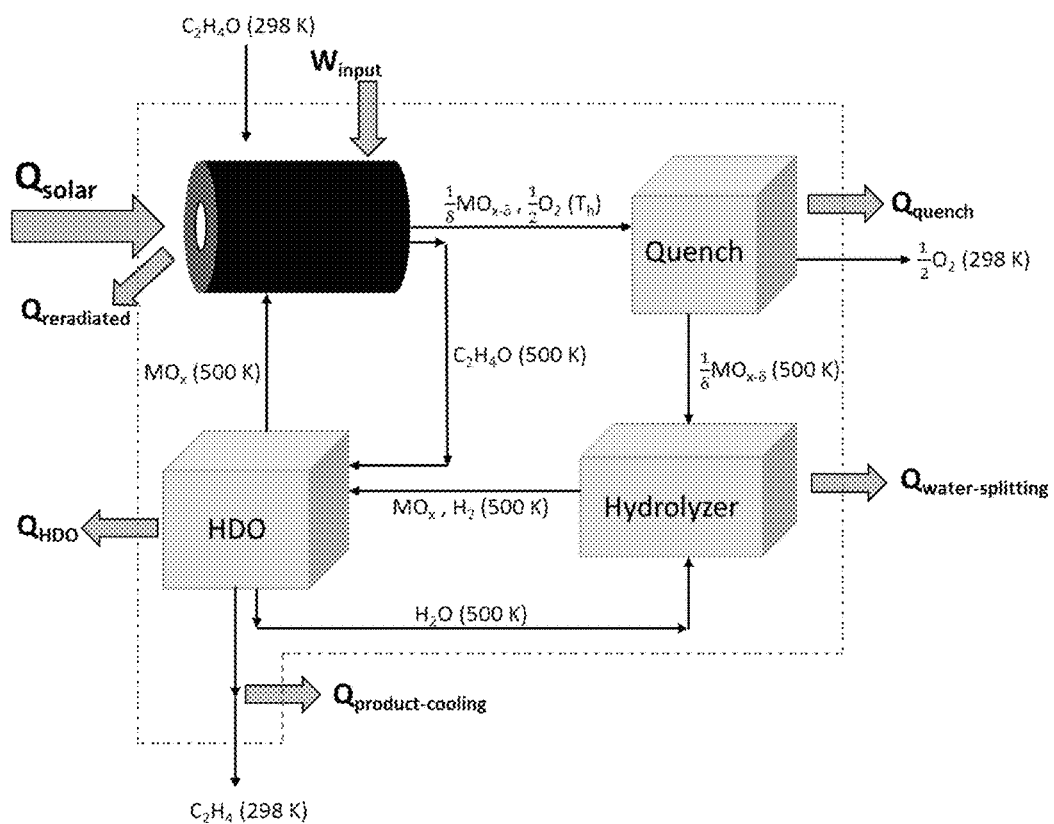
FIG. 5 is a model flow diagram of the solar thermal upgrading of acetaldehyde to ethylene used in the exergy analysis.
Figure 6:
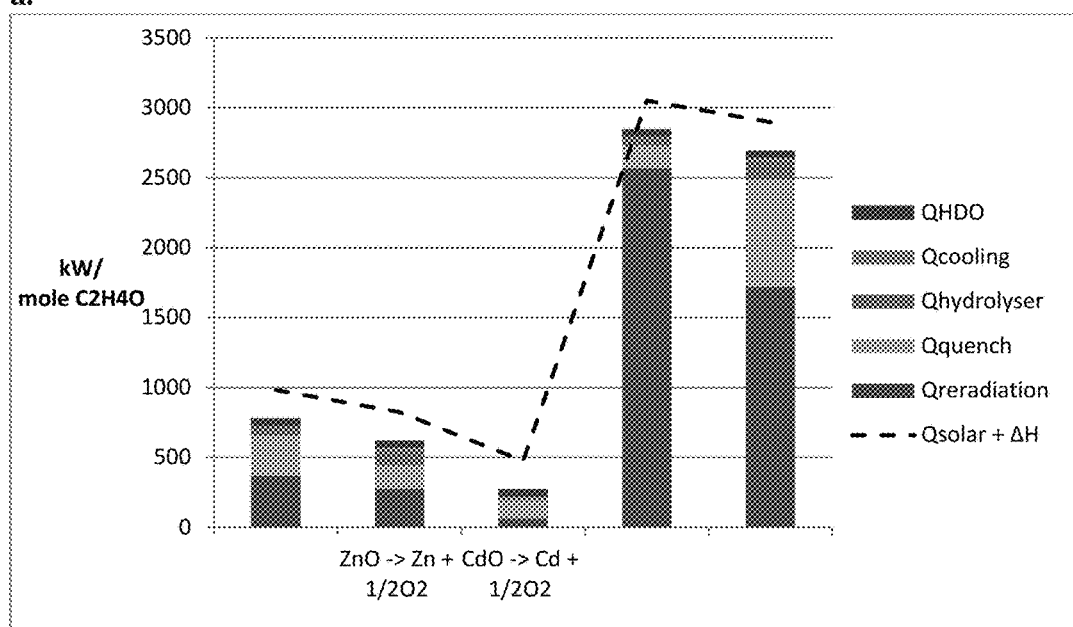
FIGS. 6a and 6b are graphs of sources of heat loss in the exergy model for acetaldehyde upgrading to ethylene.
Figure 6:
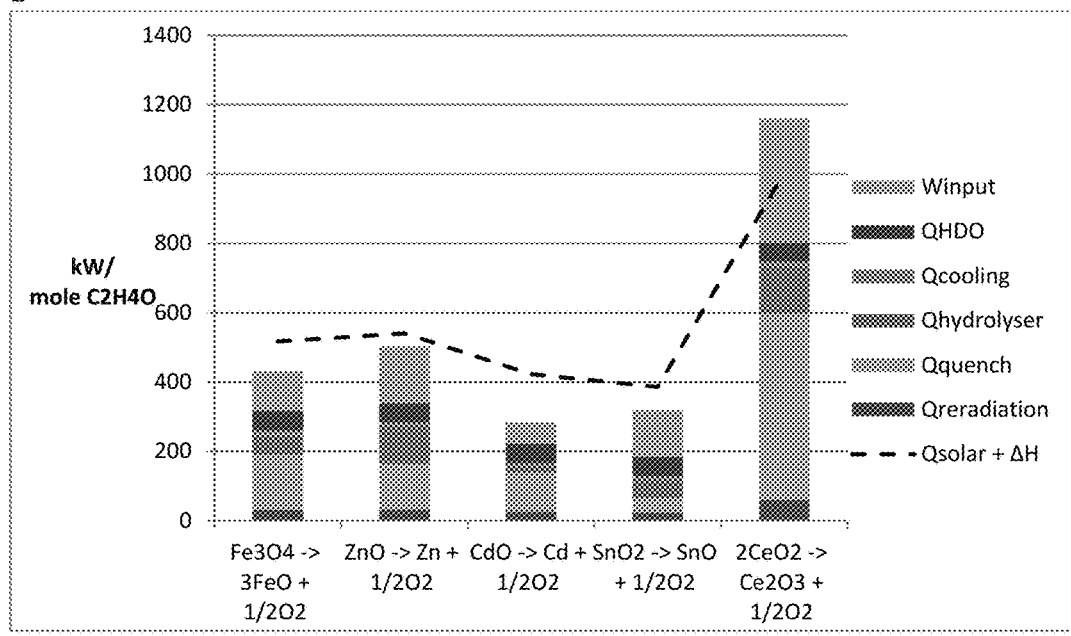

Referring to FIG. 5, a model flow diagram is provided of the solar thermal upgrading of acetaldehyde to ethylene used in the exergy analysis. A model flow diagram for the proposed TC is presented in FIG. 5. This schematic set up consists of a solar furnace for thermal reduction of the metal oxide, a quenching or cooling device, a hydrolyzer reactor for the splitting of water via re-oxidation of the reduced oxide, and finally an HDO reactor in which acetaldehyde is hydrodeoxygenated to ethylene with $H_2$ from the hydrolyzer.

The cycle begins with the solar heating of acetaldehyde to 500 K and the solar heating of the metal oxide to $T_h$ followed by dissociation to the reduced oxide and oxygen gas. Two scenarios are analyzed, representing different operating conditions within the solar furnace. In the first scenario (pure thermal dissociation) $T_h$ is set equal to the dissociation temperature, $T_d$, of the oxide, defined as the temperature at which reduction of the oxide to its low valence state (Equation 7) becomes exergonic. In the second scenario, $T_h$ is set equal to 1500 K and additional work is added to the solar reactor (i.e. via electrothermal reduction, vacuum thermal reduction, etc.) to drive the reduction of the oxide. For the first scenario, a concentration ratio of C=5000 is assumed while for the second scenario the optimum value from the previous section (C=4920) is used; in both scenarios all steps are assumed to take place at 1 bar of pressure.

TABLE 3.2

Exergy analysis of candidate oxide thermochemical upgrading cycles

| | | | Thermal Dissociation | | Reduction at 1500K | |
|---|---|---|---|---|---|---|
| Cycle | Reaction Set | $T_d$ (K) | $Q_{solar}$ (kW/mol $H_2$) | $\eta_{exergy}$ | $Q_{solar}$ (kW/mol $H_2$) | $W_{input}$ (kW/mol $H_2$) | $\eta_{exergy}$ |
| 1 | $Fe_3O_4 \to 3FeO + \frac{1}{2}O_2$<br>$3FeO + H_2O \to Fe_3O_4 + H_2$<br>$C_2H_4O + H_2 \to C_2H_4 + H_2O$ | 2383 | 1005 | 0.20 | 540 | 116 | 0.16 |
| 2 | $ZnO \to Zn + \frac{1}{2}O_2$<br>$Zn + H_2O \to ZnO + H_2$<br>$C_2H_4O + H_2 \to C_2H_4 + H_2O$ | 2320 | 846 | 0.24 | 563 | 163 | 0.067 |
| 3 | $CdO \to Cd + \frac{1}{2}O_2$<br>$Cd + H_2O \to CdO + H_2$<br>$C_2H_4O + H_2 \to C_2H_4 + H_2O$ | 1843 | 499 | 0.40 | 445 | 62 | 0.31 |
| 4 | $SnO_2 \to SnO + \frac{1}{2}O_2$<br>$SnO + H_2O \to SnO_2 + H_2$<br>$C_2H_4O + H_2 \to C_2H_4 + H_2O$ | 2930 | 3073 | 0.066 | 409 | 133 | 0.17 |
| 5 | $2CeO_2 \to Ce_2O_3 + \frac{1}{2}O_2$<br>$Ce_2O_3 + H_2O \to 2CeO_2 + H_2$<br>$C_2H_4O + H_2 \to C_2H_4 + H_2O$ | 2684 | 2918 | 0.069 | 1026 | 357 | 0 |

After reduction in the solar furnace, the reduced oxide and oxygen are cooled to 500 K. For the candidate oxides with gaseous or metastable reduction products; namely Zn, Cd, FeO and SnO, this cooling step must involve rapid quenching to avoid recombination with oxygen. Therefore, no heat is recovered during quenching or cooling of products. In the next step, the reduced oxide is sent to the hydrolyzer reactor where it is re-oxidized by water, rejecting additional heat from the cycle and producing $H_2$. These reactants are then sent on to the HDO reactor where they encounter acetaldehyde, which has been brought up to temperature by heating in the solar furnace. Hydrodeoxygenation of acetaldehyde generates additional heat and forms water, which is recycled to the hydrolyzer, and ethylene, which exits the TC after cooling to 298 K. By considering only the inputs and outputs to the cycle enclosed in the dotted line in FIG. 4, it is easy to see that the net result of the cycle is the reduction of acetaldehyde to form ethylene and oxygen via the input of solar heat.

$$C_2H_4O \to C_2H_4 + \frac{1}{2}O_2 \quad (15)$$

Therefore, the exergy efficiency of the process may be defined as:

$$\eta_{exergy} = \frac{\dot{n}_{C_2H_4O}\Delta G_{298\ K}\big|_{C_2H_4O \to C_2H_4 + \frac{1}{2}O_2} - \dot{W}_{input}}{\dot{Q}_{solar}} \quad (16)$$

Here $\dot{n}_{C_2H_4O}$ denotes the molar flow rate of acetaldehyde through the reactor, which is set equal to 1 mole/second and the $\Delta G$ term refers to the Gibbs energy change of the deoxygenation of one mole of acetaldehyde at 298 K. $\dot{W}_{reduction}$ represents the additional work provided to the solar furnace to drive the oxide reduction reaction (this term is equal to zero when $T_{reduction} = T_d$). $\dot{Q}_{solar}$ is the solar heat supplied to the reactor, and is given by the quotient of the total heat required by the solar reactor, $\dot{Q}_{reactor,\ net}$, and the absorption efficiency, which is defined in Equation 12.

$$\dot{Q}_{solar} = \frac{\dot{Q}_{reactor,net}}{\eta_{absorption}} \quad (17)$$

The term $\dot{Q}_{reactor,\ net}$ accounts for the heating and enthalpy of reaction of the oxide reduction as well as the heating of acetaldehyde to 500 K.

$$\dot{Q}_{reactor,net} = \dot{n}_{MO_x}\Delta H\big|_{MO_x(298\ K) \to MO_{x-\delta} + \frac{\delta}{2}O_2(T_h)} \quad (18)$$
$$+ \dot{n}_{C_2H_4O}\Delta H\big|_{C_2H_4O(298\ K) \to C_2H_4O(500\ K)}$$

Here, $\dot{n}_{MO_x}$ is the molar flow rate of metal oxide into the solar reactor, which is set equal to $1/\delta$ moles/second in order to balance the flow of acetaldehyde into the reactor. The results of this analysis are presented in Table 3.2.

We have also calculated the value of each heat loss term illustrated in FIG. 5 for the five candidate cycles. Decomposing the heat transfer out of the TC into its constituent parts allows for a comparison of the relative contribution of each Q term. This is illustrated for the pure thermal dissociation case ($T_h = T_d$, $W_{input} = 0$) in FIG. 6a and for the work-added case ($T_h = 1500$ K, $W_{input} \neq 0$) in FIG. 6b. The height of each bar, $\dot{Q}_{loss}$, is given by the sum of each heat loss term plus the work added during reduction of the metal oxide:

$$\dot{Q}_{loss} = \dot{Q}_{reradiated} + \dot{Q}_{quench} + \dot{Q}_{water\text{-}splitting} + \dot{Q}_{HDO} + \dot{Q}_{product\text{-}cooling} + \dot{W}_{input} \quad (19)$$

Referring to FIGS. 6a and 6b, sources of heat loss in the exergy model for acetaldehyde upgrading to ethylene. Referring to FIG. 6a, pure thermal reduction ($T_h = T_d$, $W_{input} = 0$) is provided. Referring to FIG. 6b, work added during reduction ($T_h = 1500$ K, $W_{input} \neq 0$) is provided.

Furthermore, by a Second Law balance:

$$\dot{Q}_{solar} = \dot{Q}_{loss} - \dot{n}_{C_2H_4O}T_c\Delta S_{298K}\big|_{C_2H_4O \to C_2H_4 + \frac{1}{2}O_2} \quad (20)$$

Therefore the net work done by the cycle in deoxygenating acetaldehyde to ethylene is:

$$\dot{W}_{net} = \dot{n}_{C_2H_4O}\Delta G_{298K}\big|_{C_2H_4O \to C_2H_4 + \frac{1}{2}O_2} - \dot{W}_{input} = \quad (21)$$
$$\dot{Q}_{solar} + \dot{n}_{C_2H_4O}\Delta H_{298K}\big|_{C_2H_4O \to C_2H_2 + \frac{1}{2}O_2} - \dot{Q}_{loss}$$

This quantity is illustrated in FIGS. 6a and 6b by the distance between the dotted line and the top of each bar. In the work-added case for the $Ce_2O_3/CeO_2$ cycle, $W_{net}$ is a negative quantity, leading to the exergy efficiency of zero reported in Table 3.2.

For the pure thermal dissociation of oxides with a high value of $T_d$, especially $SnO_2$ and $CeO_2$, re-radiation losses from the solar reactor account for the majority of heat lost from the system. For the work-added scenario, the re-radiation losses are actually quite small, with the majority of heat loss occurring during the quenching or cooling step. We have assumed here that no quenching or cooling heat is recovered; typical quenching parameters make any heat recovery difficult. Low-temperature heat lost during the water-splitting reaction, the HDO reaction and product cooling constitutes a relatively small component of the total heat loss, and has also been assumed non-recoverable. In practice, a small amount of pumping work will be required due to pressure drops occurring between the stages of the cycle. Additionally, very-rapid quenching conditions, as are sometimes employed in Zn/ZnO thermochemical cycling, may necessitate the addition of work for rapid cooling and recirculation of carrier gas. We have based our calculations complete conversion of reactants to products in each step of the cycle as justified by the equilibrium model presented herein.

In the upgrading scheme, the water-splitting reaction and the HDO reaction would occur simultaneously in the same reactor rather than separately in a hydrolyzer and an HDO reactor, as is the case for the flow scheme used in the exergy analysis. One might speculate, therefore, that the deoxygenation of feedstock oxygenates such as acetaldehyde could occur by a direct interaction of the oxygenate compound with the metal oxide surface without requiring the formation of gas-phase $H_2$. Therefore the analysis presented in this section represents a lower bound for exergy efficiency; if the direct deoxygenation of oxygenates could be achieved, more easily reduced oxide cycles such as NiO and CoO may be employed, leading to an improved TC exergy efficiency.

In the upgrading scheme, the bulk-reduced oxide acts as a well of reduction potential, which is drawn upon by reactions occurring at the surface until the bulk-reduced oxide is completely re-oxidized and the bulk reduction potential is exhausted. Until now, we have assumed that the formation of gas-phase $H_2$ is a necessary step in the overall upgrading process. A more likely route, however, is the direct deoxygenation of feedstock oxygenates on the metal oxide surface. This might occur by any of the reaction mechanisms familiar to traditional HDO. In general, the mechanisms by which traditional HDO occurs may be lumped into two categories. In the first, which is descriptive of oxide, sulfide, and reducible oxide catalysts like $MoO_3$, $WO_3$, and $Cr_2O_3$, HDO occurs by the formation of a surface oxygen vacancy or sulfur vacancy upon reaction with $H_2$ (forming $H_2O$ or $H_2S$), followed by the abstraction of an oxygen atom from a feedstock oxygenate into the surface coordinatively unsaturated site, refilling the lattice vacancy. This is essentially the reverse process of selective oxidation, for which an extensive body of literature exists. In the second mechanistic category, which relates to supported transition metal catalysts, $H_2$ dissociatively adsorbs on the transition metal surface while feedstock oxygenates are adsorbed on the support. Spill-over of adsorbed hydrogen to the support leads to HDO of oxygenates where the supported transition metal surface may also play the dual role of stabilizing adsorbed oxygenates (particularly carboxylic acids) during the surface reaction.

Figure 7:
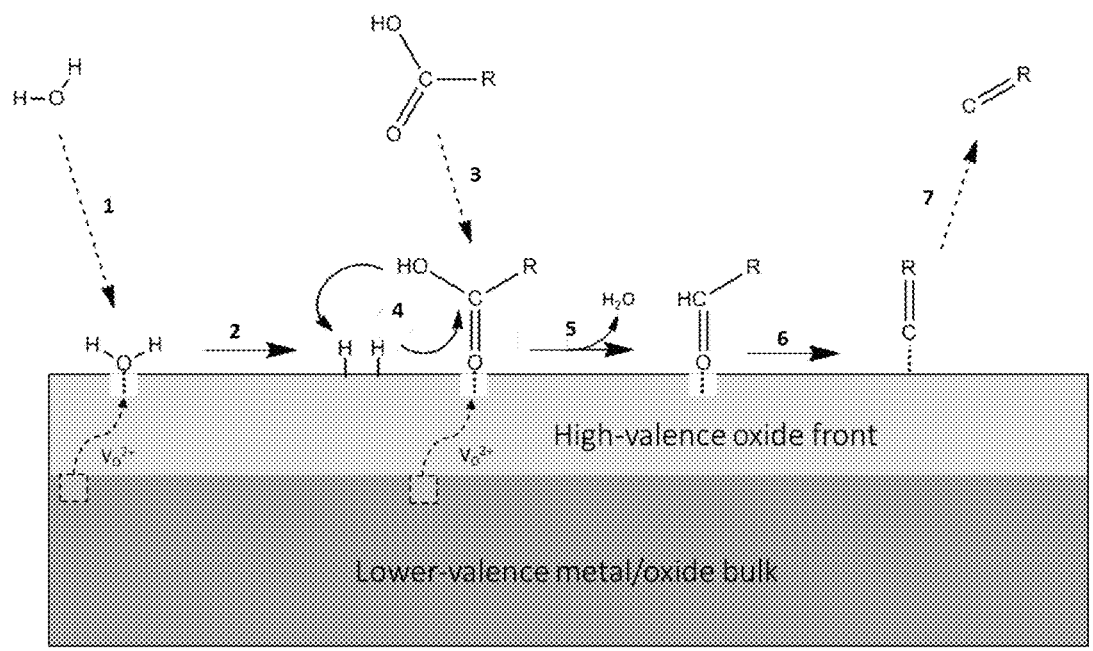
FIG. 7 is a schematic view of generalized mechanism of carboxylic acid upgrading over a bulk-reduced oxide catalyst.
Figure 8:
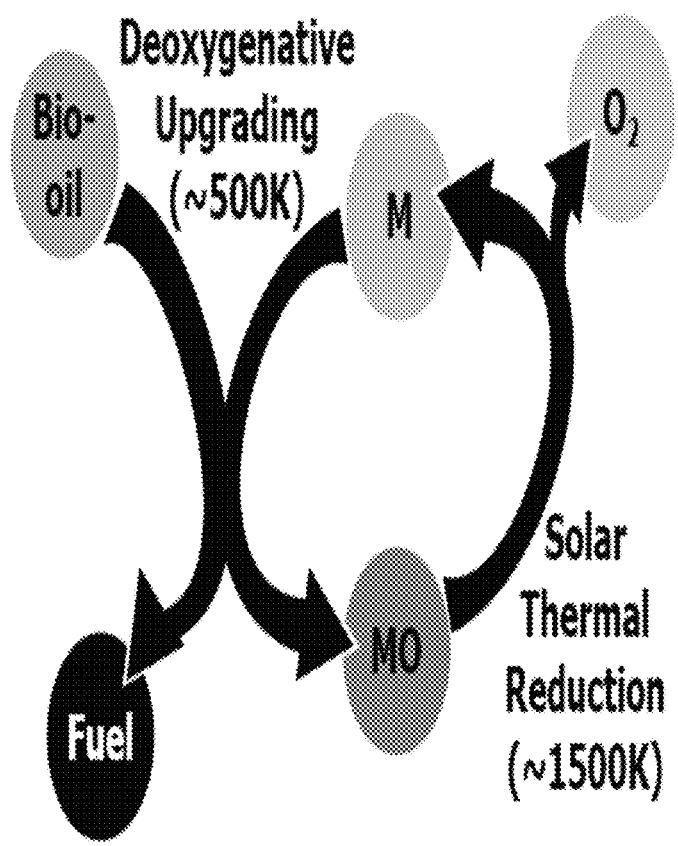
FIG. 8 is schematic view of another embodiment of the looped-oxide catalysis (LOC) thermochemical cycle for bio-oil feed stock deoxygenation.

Referring to FIG. 7, a generalized mechanism of carboxylic acid upgrading over a bulk-reduced oxide catalyst is provided. The kinetics of looped oxide catalysis differ from traditional HDO in the source of surface hydroxyls and oxygen vacancies; in traditional HDO these derive from the adsorption and oxidation of gas-phase $H_2$ on the catalyst surface, whereas in the proposed scheme these derive from the oxidation of the reduced bulk. Namely, the formation of surface hydroxyls and oxygen vacancies depends on the bulk diffusion processes (primarily the bulk migration of oxygen anion and metal cation interstitials and vacancies) occurring between the metal-oxide interface and the surface. A generalized illustration of the coupled bulk diffusion processes and a few of the possible surface reaction mechanisms is given in FIG. 7. This illustration shows how reactions occurring at the surface lead to the formation of a high-valence oxide front, which expands into the metallic or low-valence oxide bulk as reactions on the surface progress. In step (1), chemisorption of a water molecule results from the Lewis acid-base interaction of the oxygen lone pair with a coordinatively unsaturated surface metal cation, which derives from the bulk migration of an oxygen vacancy from the metal-oxide interface. The diffusion of oxygen vacancies towards the surface is accompanied by interstitial diffusion of oxygen anions from the surface towards the metal-oxide interface, as well as the diffusion of metal cation interstitials and vacancies (not shown); the diffusion mechanism responsible for oxidation will depend on the structure of the metal oxide considered. The dissociative adsorption of the water molecule leads to the formation of two surface hydroxyls, as shown in step (2). In step (3) the carbonyl oxygen lone pair of a carboxylic acid chemisorbs to a second surface Lewis acid site, which also derives from the bulk diffusion of an oxygen vacancy from the metal-oxide interface. This is followed by the hydrogenation of the carboxylic acid hydroxyl group producing (5) a water molecule and an adsorbed aldehyde. In final surface step (6), carbon-oxygen bond of the aldehyde carbonyl group is cleaved and the oxygen is abstracted into the lattice of the high-valence oxide front while the reduced product alkene desorbs (7).

The previous identification of looped oxide cycles was based on bulk thermodynamics and diffusion characteristics of the oxides. The catalytic performance of such an oxide towards feedstock upgrading, however, will depend on surface thermodynamics and kinetics. The chemisorption of oxygenates onto an oxide catalyst depends on the Lewis acid-base interaction between coordinatively unsaturated metal ion surface sites and the oxygen lone pair in the feedstock oxygenate; at the same time proton donation to the adsorbed species depends on the Brønsted acidity of surface hydroxyls. An effective catalyst should have sufficiently strong surface Lewis acid sites to cleave the oxygenate C—O bond upon abstraction of the oxygen onto the surface vacancy. Additionally the surface must be able to accommodate a sufficient concentration of oxygen vacancies without undergoing structural collapse[91]. Finally, the deoxygenation and hydrogenation of adsorbed species should be selective; saturation of carbon double bonds in feedstock oxygenates is undesirable because it leads to oxidation of the reduced oxide bulk without a corresponding deoxygenation of the adsorbate. Finding a single metal oxide redox pair with desirable bulk thermodynamics and diffusion kinetics in addition to desirable surface kinetic and acid-base properties may be difficult. A more realizable goal, therefore, may be the integration of bulk-reduced metal oxides as supports for traditional HDO catalysts like NiMo or CoMo, or else as a support for the more recently-developed reducible oxide catalysts like $WO_3$ and $MoO_3$ which are capable of sustaining higher concentrations of surface vacancies. Of course, such a supported catalyst must be able to repeatedly undergo the high-temperature reduction step without sustaining significant chemical or morphological change.

The direct deoxygenation of feedstock oxygenates by bulk-reduced oxides via looped-oxide catalysis offers four distinct advantages over traditional HDO:

1. Traditional HDO typically requires a high pressure (typically 100-200 bar) and a high partial pressure of exogenous $H_2$, well in excess of the stoichiometrically specified amount. The high partial pressure of $H_2$ is argued to increase the reaction rate and decrease catalyst coking by occasioning a higher availability of hydrogen in the vicinity of the catalyst. For example, the prior art uses hydrogen in excess of 35-420 moles H2 per kg bio-oil, compared to a required amount of 25 moles/kg for complete deoxygenation. The first improvement of the proposed scheme over traditional HDO results from achieving a high availability of hydroxyl groups and coordinatively unsaturated metal sites on the oxide surface without requiring a high partial pressure of $H_2$, since these surface reducing agents derive from within the reduced bulk of the oxide. Significant efficiency savings could also be achieved by utilizing looped oxide catalysis for feedstock upgrading at ambient pressure.

2. The deoxygenation and hydrogenation reactions involved in hydroprocessing (equation 3, for example) tend to be fairly exergonic. This often means that a considerable portion of the exergy expended in generating the $H_2$ is never recovered. This is avoided in the proposed scheme by utilizing a reduced oxide catalyst whose reduction potential is not strong enough to split water, but is strong enough to generate surface Lewis acid sites capable of performing HDO. The resulting exergy savings would be claimed during the reduction step, which for such a cycle requires less input of energy solar and external energy.

3. During traditional HDO processes, both surface hydroxyls and oxygen vacancies derive from the adsorption or reaction of the catalyst with gas-phase $H_2$. In the case of bulk-reduced oxide catalysts, however, surface hydroxyls derive primarily from the adsorption and reduction of $H_2O$ in a Lewis acid-base reaction. Therefore, the use of bulk-reduced oxide catalysts allows for control over which mechanism dominates the reaction by determining the ratio of surface hydroxyls to surface coordinatively unsaturated Lewis acid sites through altering the composition (particularly the water content) of feedstock.

4. An additional benefit of the proposed scheme is that the catalyst is renewed upon each iteration of the TC, avoiding the significant problem of long-term catalyst coking, which is prevalent in traditional HDO processes.

It has been presented a novel scheme for the upgrading of low-quality bioliquids through the use of bulk-reduced metal oxide catalysts as part of a two-step solar thermochemical cycle. This fuel upgrading path enjoys several potential efficiency gains over traditional HDO, particularly if the surface reactions can be tailored to occur directly between surface-bound oxygenate adsorbates and surface hydroxyls and coordinatively unsaturated sites without the formation of gas-phase $H_2$. The field of solar-thermal processing is now mature to the extent that the use of solar thermochemical cycles for bioliquid upgrading is feasible and merits exploration. There are many more metal oxides redox cycles with acceptable bulk thermodynamics than the five candidates identified in this analysis. A thorough understanding of the characteristics of deoxygenation over each possible oxide (acting as a catalyst or support), obtained through the coupling of electronic structure calculations and experimental kinetic and surface studies, will allow for greater precision in selecting and modeling fuel upgrading reactions over bulk-reduced oxide catalysts.

Referring generally to FIGS. 8-13, the invention, in another embodiment, incorporates the advantages and benefits of the above-mentioned invention, further relates in general to an integrated thermochemical process, also known as looped oxide catalysis, for providing an upgraded biofuel composition from a feedstock.

A critical step in the conversion of pyrolysis and liquefaction bio-oils to transportation fuels is deoxygenative upgrading. With this perspective we introduce a two-step thermochemical cycle which harnesses concentrated solar radiation to drive bio-oil deoxygenation. In this cycle, which we have termed "looped-oxide catalysis" (LOC), a metal oxide is reduced in a high-temperature solar thermal reactor and subsequently reacted with bio-oil, reforming the original metal oxide and yielding a deoxygenated biofuel product. By augmenting the chemical energy stored in bio-oil with solar thermal energy, LOC may increase fuel yields up to threefold for a given quantity of biomass over yields currently achievable with stand-alone biomass-to-fuel pathways. We identify five promising candidate LOC materials based on equilibrium thermo-dynamics, diffusion kinetics and catalytic performance in hydrodeoxygenation (HDO) reactions. Additionally, we present proof-of-concept experimental results and mechanistic implications from an investigation of the LOC upgrading of acetic acid. The formation of acetaldehyde with comparable selectivity in LOC with zinc metal as well as HDO with zinc oxide suggests that surface oxygen vacancies are the catalytically relevant sites in both processes.

In this perspective, we present a novel augmented biofuel production pathway which indirectly harnesses solar thermal energy to drive the deoxygenation of bio-oil. This process, which we have termed "looped-oxide catalysis" (LOC), is envisioned as a two-step thermochemical cycle, illustrated in FIG. 8. In one step of the cycle, bio-oil is upgraded by reaction with a reduced metal oxide, forming a higher-valence oxide and yielding a deoxygenated fuel product. During this upgrading step, the reduced metal oxide provides both a bulk source of reducing potential to drive the deoxygenation reaction and a catalytic surface on which the reaction may proceed, thereby promoting both the thermodynamics and the kinetics of the reaction. "Catalysis" in this context is used specifically to refer to the role of the metal oxide surface chemistry in determining the rate of formation and yield of deoxygenation products within a wider range of possible reaction products. In the opposing step of the cycle, the metal oxide is heated in a solar furnace to the point at which it dissociates to its metal or to a low-valence metal oxide and oxygen gas. We note that other processes can be envisioned to regenerate the reduced metal oxide, e.g., involving very-high-temperature nuclear reactors, carbothermal reduction or electrochemical processing, but in the current work we focus on solar thermal regeneration due to the unambiguous renewable nature and the large body of research focused on that area.

We view this process as a compliment and alternative to the hydroprocessing of bio-oil, which in most current applications is limited by requisite high $H_2$ pressures and by the destruction of chemical exergy during the reaction of $H_2$ with easily-reduced, oxygenate compounds. The coupling and integration of the solar thermal reduction of metal oxides to the direct deoxygenation of bio-oil forms a complete thermochemical cycle.

The successful performance of any looped-oxide catalysis (LOC) thermochemical cycle is predicated on the fulfillment of at least three criteria:

(1) The thermodynamics of the cycle must permit the deoxygenation of bio-oil oxygenates at the temperature of the upgrading reaction while minimizing the energetic cost of the high-temperature thermal or electrothermal reduction step;

(2) Each reaction step must proceed at an acceptable rate, notably including the diffusion of oxygen through the higher-valence oxide surface during the upgrading reaction; and (3) The higher-valence metal oxide surface formed during the upgrading step must function as a catalyst for the LOC deoxygenative upgrading reaction, where successful performance in HDO reactions is seen as an indicator of potential activity in LOC. In addition to these three constraints, consideration should be given to the cost and nature of any separation steps and to the weight, toxicity and the global availability of the candidate LOC oxide material. Herein, we evaluate several candidate TCs based on these criteria.

Because the objective of LOC is the deoxygenation of bio-oil oxygenates compounds, the thermodynamic performance of this process in conjunction with the thermal reduction of a metal oxide is considered the primary criterion in candidate LOC cycle selection. In developing an effective metric for optimizing the selection of LOC materials we turn to an analogue in catalysis: the Sabatier Principle states that the interaction between a catalyst and its substrate should be neither too strong (the substrate will not desorb, blocking catalytic sites) nor too weak (the substrate will not adsorb and no reaction will occur). This concept is often invoked in catalyst engineering to create a "volcano plot" where the activities of different catalysts are plotted against the substrate binding energy or any other parameter pertaining to the catalyst's ability to form bonds with the substrate. The Sabatier Principle may also be applied to looped-oxide catalysis: the reduced oxide should have an oxygen affinity that is sufficiently high to abstract oxygen atoms from the bio-oil oxygenate species, but also sufficiently low that the higher-valence oxide may be reduced in the solar furnace with a minimum input of heat and work.

Figure 9:
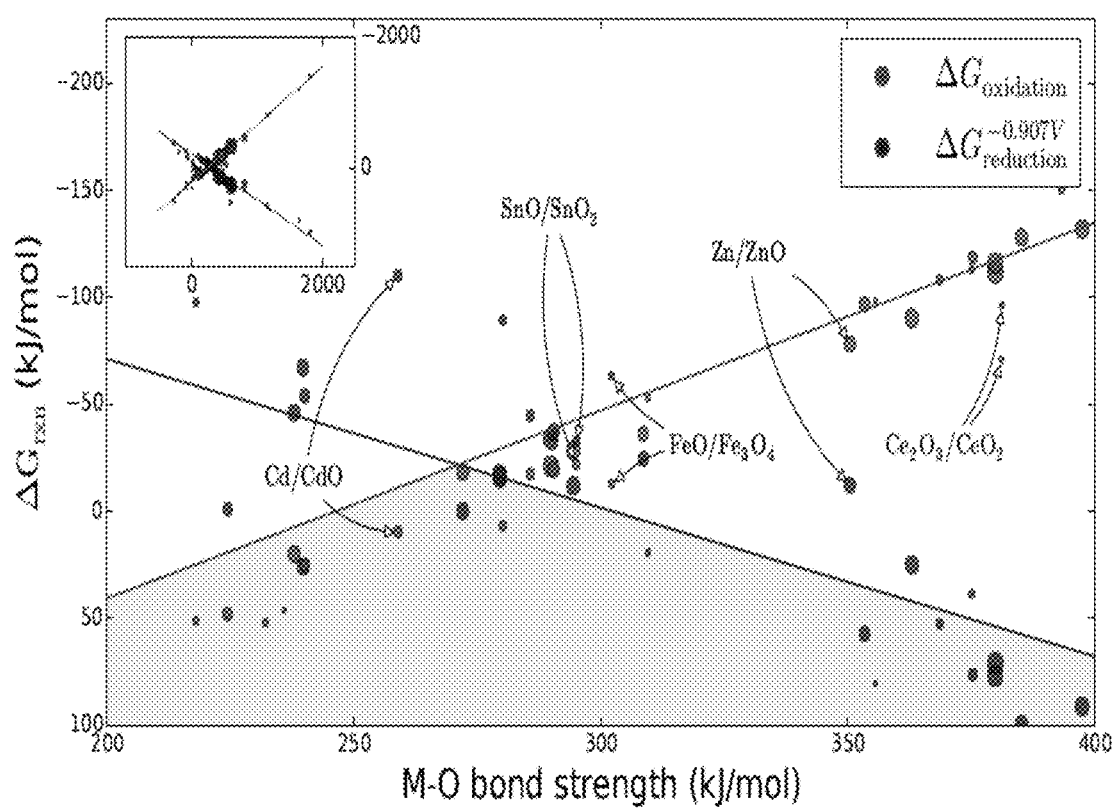
FIG. 9 is a graph showing a Volcano-type plot of looped-oxide catalysis (LOC) cycles with five candidate cycles annotated.

Referring to FIG. 9, volcano-type plot of LOC cycles is provided, with the five candidate cycles annotated. Red and blue points represent, respectively, the ΔG of the reduced oxide reaction with acetic acid at 500 K in kJ/mole acetic acid (Equation 6) and ΔG of the solar thermal reduction at 1500 K and −0.907 V in kJ/1 mole O2 (Equation 4), plotted against ΔH of reduction at 500 K in kJ/1 mole O2, which is used as a measure of the metal-oxygen bond strength. The inset figure depicts the volcano-type plot over its entire range of the 80 cycles included in this analysis. The red and blue functions are linear regressions for the plotted data points. The weight of each data point corresponds to the mass of oxide per mole of acetaldehyde generated; a larger dot indicates a greater yield of acetaldehyde per mass of oxide. The full data set is available in the supplementary information.

Thermochemical data is utilized from the Barin and JANAF tables to identify desirable looped-oxide materials; that is, thermodynamically feasible pairs of metal oxides and their reduction products (either low-valence oxides or zero-valent metals). Bio-oil contains a diverse range of oxygenate compounds, all of which may undergo deoxygenation through numerous reaction pathways. To make the analysis of looped-oxide catalysis (LOC) tractable, we have chosen acetic acid, $CH_3COOH$, as a model bio-oil oxygenate compound. Lower carboxylic acids are a common component of bio-oils, constituting 5-10 wt % of a typical bio-oil sample. The deoxygenation of carboxylic acids is also a useful benchmark reaction because the high acidity of bio-oils (pH of 2-3) renders bio-oils unstable and corrosive. Finally, the hydrodeoxygenation (HDO) of acetic acid to acetaldehyde is well-characterized over a wide range of metal oxide catalysts. The LOC reduction of acetic acid to acetaldehyde, as represented in the reaction below, is therefore utilized as a model reaction for bio-oil deoxygenation.

(6)

In FIG. 9, the Gibbs free energy of thermal reduction and the Gibbs free energy of re-oxidation by reaction with acetic acid is plotted for eighty LOC cycles against the corresponding enthalpy of reduction, which is used as a metric of oxygen binding strength. The numeric values of thermodynamic quantities and reaction stoichiometries are provided in Appendix C of the Supporting Information. While the entire volcano is shown in the inset, the main figure highlights a detail of the volcano "peak" where the most thermodynamically-desirable metal oxide redox cycles exist, i.e. those with intermediate metal-oxygen bond strength. In this proxy analysis, it is assumed that the oxidation step takes place at 500 K and 1 bar and that the regeneration step takes place at 1500 K, 1 bar, and at a reduction potential of –0.907 V. This is the potential necessary to make the reduction of FeO to Fe exergonic at 1500 K. This was chosen as a benchmark potential because the FeO/Fe cycle has the lowest ΔH of reduction of all LOC cycles which achieve exergonic deoxygenation acetic acid at 500 K. It is also assumed that all oxides step sequentially through oxidation states during redox reactions and that discrete oxidation states exist for all oxides according to the stoichiometric values in the source of thermochemical data.

The thermochemical analysis identifies a number of appealing LOC cycles, many of which are the same cycles that have demonstrated success in solar thermochemical water-splitting. A number of suitable materials are provided herein—FeO/Fe3O4, Zn/ZnO, Cd/CdO, SnO/SnO2 and Ce2O3/CeO2—and discuss these materials in the context of their oxygen diffusion kinetics and performance as hydrodeoxygenation (HDO) catalysts. Of course, it is contemplated that other low-valence metal oxides, zero-valent metals, or high-valence metal oxides, and other mixtures, combinations, and variations thereof, may be used in accordance with parameters or requirements discussed herein.

$FeO/Fe_3O_4$

Beyond its desirable thermodynamics, the principal advantages of iron oxide systems are low cost and high availability of materials. Another notable feature of iron oxide systems is the potential for partial substitution in $FeO/Fe_3O_4$ by distinct metal oxides of the form $MO/M_3O_4$ to achieve more desirable thermochemical, kinetic and material properties in the formed ferrite material. Ferrites such as $Ni_{0.5}Mn_{0.5}Fe_2O_4$ and $CuFe_2O_4$ have been studied in thermochemical cycling applications both in the partially-substituted spinel crystal phase and in ferrites synthesized through atomic layer deposition of alternating layers of, e.g., $Fe_2O_3$ and CoO to achieve a bulk layered cobalt ferrite, $CoFe_2O_4$. The limiting factor in the kinetics will likely be due to the rate of diffusion of oxygen into the bulk of the metal. Also within the solar thermochemical community, recovery of process heat has proven difficult as quenching has been employed to avoid recombination of FeO with O2 upon reduction. The rapid quenching to non-stoichiometric and nearly-stoichiometric wüstite, e.g. $FeO_{0.982}$, is often desirable as the oxidation of these phases by water is much more rapid than that of stoichiometric FeO due to the high presence of bulk defects. Iron oxide has demonstrated catalytic ability in HDO; interestingly, its highest selectivity (up to 80%) in the vapor-phase hydrodeoxygenation of acetic acid to acetaldehyde was reported when iron is present in both its oxide and metallic phases, as may be expected in some stages of an LOC process.

Zn/ZnO.

An intriguing cycle for LOC upgrading of bio-oil is Zn/ZnO. This cycle can exhibit very high exergy efficiency due to the relatively low heat capacity of ZnO, while achieving high stoichiometric deoxygenation per mass of Zn. The thermal dissociation of ZnO to Zn was recently demonstrated with success in a 100 kWth pilot plant which yielded condensed products with a Zn molar fraction of up to 49%. As with the $FeO/Fe_3O_4$ cycle, the rate of diffusion of oxygen interstitials and vacancies through ZnO may be expected to limit the kinetics; however, a means of achieving high (>50%) oxidation yields has been to employ Zn nanoparticles (diameter <100 nm), which may be synthesized from Zn vapor in the regeneration step. Indeed, care must be taken in the cooling of the Zn vapor to achieve good Zn metal recovery and avoid recombination with oxygen. In practice, regulation of quenching parameters following the regeneration step allows for good control over material properties including particle size of the Zn metal, which will affect both its internal mass transfer limitations as well as its catalytically active surface area. Another approach to regeneration is to conduct the reduction of ZnO in a thermal electrolytic cell at above the boiling point of Zn; this results in the evolution of gaseous Zn metal at the cathode and oxygen at the anode, a simple separation step that allows for greater flexibility in the Zn metal quenching conditions without recombination of products upon cooling Reduction of ZnO by "quasi-electrolysis" has also been suggested, wherein a supersaturated solution of ZnO is heated in an electrolytic cell to a temperature at which reduction is exergonic but maintained at high-pressure to suppress spontaneous dissociation. Low-voltage electrolysis of the solution then evolves gaseous Zn and O2 at separate electrodes and the electrical energy supplied simply becomes the energy of unmixing of gaseous Zn and O2, about 19 kJ. Catalytically, ZnO exhibited activity towards the selective deoxygenation of acetic acid to acetaldehyde with a peak selectivity of 20% occurring at 338° C. ZnO has also demonstrated activity towards hydrogenation of aromatic carboxylic acids. In particular, ZnO has been shown to catalyze the hydrodeoxygenation of benzoic acid to benzaldehyde with high yields of around 90% at 350° C., and with additional deoxygenation to toluene occurring at 380° C.

Cd/CdO

Of the five candidate oxides, cadmium oxide exhibits the lowest thermodynamic barrier to reduction. As with zinc oxide, the Cd/CdO cycle requires a quenching step after reduction. Although recombination with oxygen during the quenching process may lead to a loss in cadmium metal recovery, an electrolytic set-up may be utilized to achieve separation. It may also be possible to bypass diffusion limitations inherent to other metal oxide TCs by carrying out the re-oxidation of cadmium in its molten liquid state. The toxicity of cadmium, however, limits its prospects for fuel upgrading and also dictates the role of process byproducts such as waste mineral ash. To our knowledge cadmium oxide has not been investigated as a catalyst for bio-oil deoxygenation; however, previous research has demonstrated the activity of CdO as a Lewis-acid catalyst for the hydrolysis, esterification and transesterification of triglycerides and fatty acids in bio-diesel production.

$SnO/SnO_2$

SnO is metastable at temperatures above 600 K and will disproportionate into Sn and SnO2. As with the non-stoichiometric wüstite phases in the iron oxide cycle, fast oxidation kinetics have been observed for the hydrolysis of SnO with no passivation effect occurring in the formed oxide surface layer. However, the oxidation kinetics of a mixture of Sn and SnO2 have been demonstrated to be slower, requiring approximately one hour of reaction time to achieve 70% conversion of micron-sized particles at 525° C.; therefore it may be preferable to suppress disproportionation as much as possible. For this reason we have based the analysis in this perspective on the formation of SnO as the reduction product. Hydroprocessing of bio-oils over $SnO_2$ catalysts has been proposed and demonstrated for the HDO of acetic acid with relatively high selectivity (40%) occurring at a temperature of 450° C. A higher selectivity of 75% was achieved when SnO2 was used as a support for platinum prepared by wet impregnation. The higher activity is attributed to the ability of platinum and other late transition metal to activate hydrogen, which may then react with acetic acid at the metal-support interface.

$Ce_2O_3/CeO_2$

Thermochemical cycles utilizing pure or doped ceria have recently demonstrated great promise for both water-splitting and CO2 reduction applications due to the high rate of oxygen vacancy migration in these materials. Fast vacancy diffusion kinetics have also made doped ceria an attractive material for solid oxide fuel cells. In solar thermochemical water-splitting, 100% conversion of mm-sized $Ce_2O_3$ particles to $CeO_2$ was observed in less than five minutes at 600° C. Thermochemical cycles involving ceria are often discussed in terms of intermediate, non-stoichiometric oxidation states, where a redox cycle has the form $CeO_{2-\delta}/CeO_2$. Values of oxygen deficiency, $\delta$, were found to range between 0.016 and 0.042 in reticulated porous ceria after solar thermal reduction at temperatures from 1400° to 1600° C. Without achieving higher oxygen deficiency, this cycle's primary limitation is the relatively low stoichiometric yield of upgraded bio-oil per mass of ceria. Catalytically, $CeO_2$ has exhibited high selectivity in the vapor-phase hydrodeoxygenation of benzoic acid to benzaldehyde at temperatures below 350° C. At temperatures above 375° C., near-complete conversion of benzoic acid was accompanied by increased formation of the more deoxygenated product toluene.

An exergy analysis of the looped-oxide catalytic upgrading of acetic acid to acetaldehyde can provide insight into the thermodynamic bottlenecks of the process as well as an assessment of the best case performance of LOC. Typical efficiency values for the five candidate LOC materials described above in an LOC process incorporating solar electrothermal reduction range from 25 to 43%, assuming no heat recovery during the quenching of solar thermal reduction products. This analysis assumes optimal optics and insulation, absorptivity and emissivity approaching unity, solar influx of 1 $kW/m^2$ and further assumes electricity for driving the electrothermal reduction is available from ideal p-n junction solar photovoltaic (PV) cells operating at the Shockley-Queisser limiting efficiency of 33.7%. The PV cell area required for the electrothermal LOC upgrading of 1 mole of acetic acid to acetaldehyde per second at ambient pressure ranges from 180 to 530 $m^2$ with the combined heliostat and PV areas ranging from 570 to 930 $m^2$.

In comparison to LOC, the efficiency of any hydrodeoxygenation (HDO) process is categorically limited by the generation and compression of $H_2$. A best-case efficiency for HDO of acetic acid to acetaldehyde with $H_2$ produced from solar photovoltaic water-splitting is roughly 30% if operated at 100 bar. This assumes hydrogen is produced from the electrolysis of water with 100% efficiency, where electricity is supplied from ideal p-n junction solar PV collection with the Shockley-Queisser limiting efficiency of 33.7%, as well as assuming complete conversion and ideal isothermal compression of $H_2$ from 1 to 100 bar. The total PV cell area required for HDO of acetic acid to acetaldehyde at a rate of 1 mole per second with H2 produced from solar electrolysis is 740 $m^2$.

The combined heliostat and PV cell areas required for the electrothermal LOC upgrading of acetic acid to acetaldehyde are in all cases below 1000 $m^2$. To put these numbers in perspective: assuming a biomass growth rate of 3 kg $m^{-2}$ $year^{-1}$ (a conservative estimate for switchgrass or poplar) and assuming the biomass can be completely represented as acetic acid in the model system, the cultivation of a sufficient amount of biomass to sustain the flow rate assigned in our calculations would require 130,000 $m^2$ of arable land. This area is two orders of magnitude greater than the area required for heliostat and photovoltaic solar collection. This illustrates how, by dedicating a relatively small portion of arable land (less than 1% of the total land area) to solar thermal and PV collection and coupling this process to the upgrading of biomass from the remainder of the land area, it may be possible to significantly increase the total fuel yield.

Experimental Investigation of LOC Upgrading Reaction

In this section, we present experimental results of an LOC upgrading reaction of zinc metal with acetic acid, which is used as a model feedstock compound for bio-oil. Of the five candidate cycles identified in the previous section, the Zn/ZnO cycle was chosen as an interesting starting point for an LOC demonstration. This cycle is considered to be one of the most promising metal oxide redox cycles for thermochemical water-splitting, given its high exergy efficiency and relatively low dissociation temperature (2320 K). Additionally, ZnO has demonstrated activity towards hydrodeoxygenation in previous studies. We have also investigated the analogous case of acetic acid hydrodeoxygenation (HDO) with a zinc oxide catalyst and will discuss the relationship between the results of these two experiments, showing that the LOC experiments can give insight on the reaction mechanisms in the HDO experiments.

Methods

Figure 10:
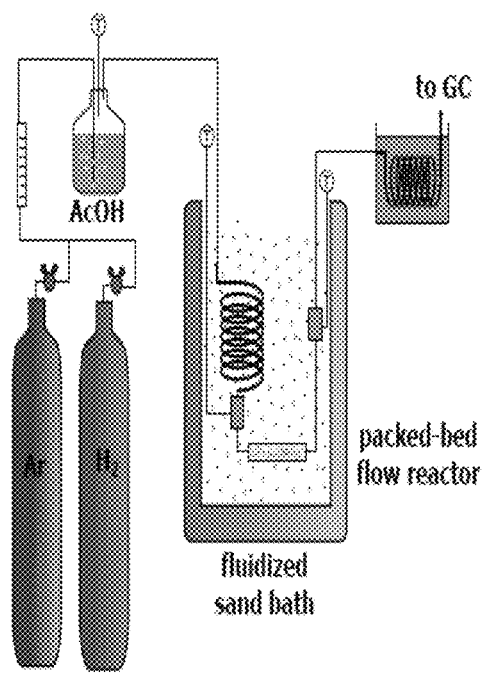
FIG. 10 is a process flow diagram of the experimental setup for the hydrodeoxygenation (HDO) and looped-oxide catalysis (LOC) upgrading of acetic acid.
Figure 11:
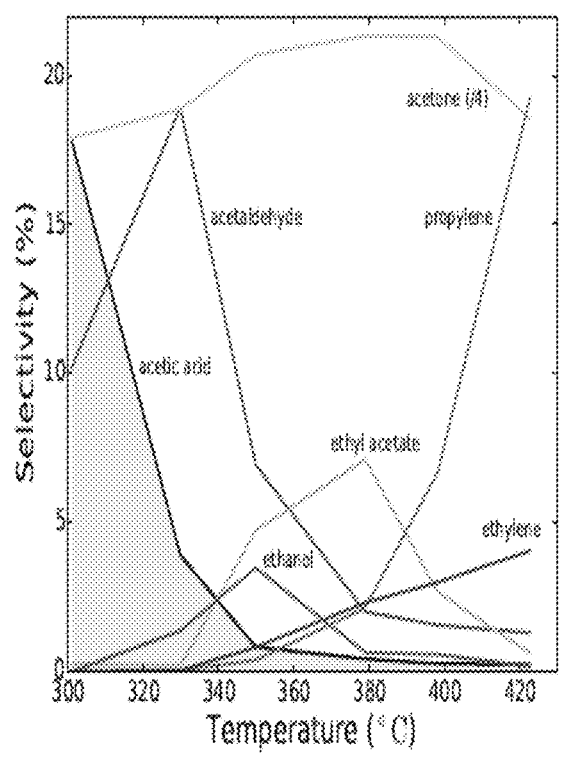
FIG. 11 is a graph of an hydrodeoxygenation (HDO) control experiment which plots the carbon-weighted selectivity as a function of temperature for acetic acid and the dominant organic products of ZnO-catalyzed hydrodeoxygenation (HDO)

The LOC upgrading of acetic acid (Fisher, 99.9%) was performed in a continuous flow reactor setup as illustrated in FIG. 10 which shows a process flow diagram of the experimental setup for the HDO and LOC upgrading of acetic acid. This setup consisted of a stainless steel 316 pre-heating coil (0.25 in. o.d., 0.02 in. wall thickness and 40 in. length) fitted to a stainless steel 316 fixed-bed reactor. Both the pre-heating coil and reactor were submerged in a heated sand bath, and temperature was monitored throughout the flow setup. An argon (PurityPlus, UHP Grade, 99.999%) gas stream with a volumetric flow rate of 45 cm3(STP)$min^{-1}$ was sparged through acetic acid at 20° C. and 1.1 bar, achieving a saturation vapor pressure of 21 mbar. The saturated argon carrier gas was then passed through a fixed-bed reactor held at 350° C. and containing 125 mmol (8.2 g) zinc metal powder (Noah Tech, 99.9%, <5 μm avg.) packed with deactivated borosilicate glass wool. The product stream was cooled and monitored quasi-continuously with an on-line gas chromatograph (Agilent 7890A) equipped with an HP-PLOT/U capillary column, flame ionization detector and thermal conductivity detector. Methane, ethylene, ethane, acetylene, propylene, propane, acetaldehyde, ethanol, acetone, ethyl acetate, acetic acid, CO2 and CO were monitored simultaneously as potential reaction products. Because of the low vapor pressure of acetic acid relative to the reaction products, all species in the product stream remained in the vapor phase and no condensate was observed.

In the analogous HDO investigation the same experimental setup and flow parameters were used but $H_2$ (PurityPlus, UHP Grade, 99.999%) replaced argon as the carrier gas and ZnO (Noah Tech, 99.999%, <5 microns avg.) was used as the catalyst, with a reactor loading of 125 mmol (10.2 g). In the HDO experiment, the temperature of the reactor was increased from 300.0 to 425.0 at a rate of PC/min with samples taken every 25 minutes. In both the HDO and LOC experiments, the catalyst surface was pretreated in H2 flow of 20 cm3(STP)min$^{-1}$ for one hour at 300° C. A carbon-weighted selectivity was calculated for the organic products using the following formula:

$$\text{Selectivity}_i(\%) = \frac{p_i C_i}{\sum_i p_i C_i} \quad (7)$$

Here pi refers to the partial pressure of a given product, i, as determined by gas chromatography and Ci refers to the number of carbon atoms in each product species.

Results

As a control experiment, we first carried out HDO of acetic acid on ZnO to facilitate validation. The selectivity toward acetic acid and dominant organic products during the ZnO-catalyzed HDO reaction is plotted in FIG. 11 which is an HDO control experiment plotted for the carbon-weighted selectivity (see Equation 7) as a function of temperature for acetic acid and the dominant organic products of ZnO-catalyzed HDO. The acetone selectivity values have been divided by four for ease of reading. These results are consistent with the literature for carboxylic acid HDO over a metal oxide catalyst. The primary byproduct of the reaction is acetone, which is produced at all temperatures via the ketonization reaction:

$$2CH_4COOH \rightarrow CH_3COCH_3 + CO_2 + H_2O \quad (8)$$

The net conversion of acetic acid to products is greater at higher temperatures. Peak selectivity to the deoxygenation product, acetaldehyde, was observed at 19% at a temperature of 325° C. The formation of ethanol is also observed at intermediate temperatures along with ethyl acetate, which has been suggested to be formed via the Fischer esterification reaction and/or the Tishchenko reaction. Finally, formation of the more-fully hydrodeoxygenated products propylene and ethylene is seen to be favored at temperatures exceeding 380° C.

Figure 12:
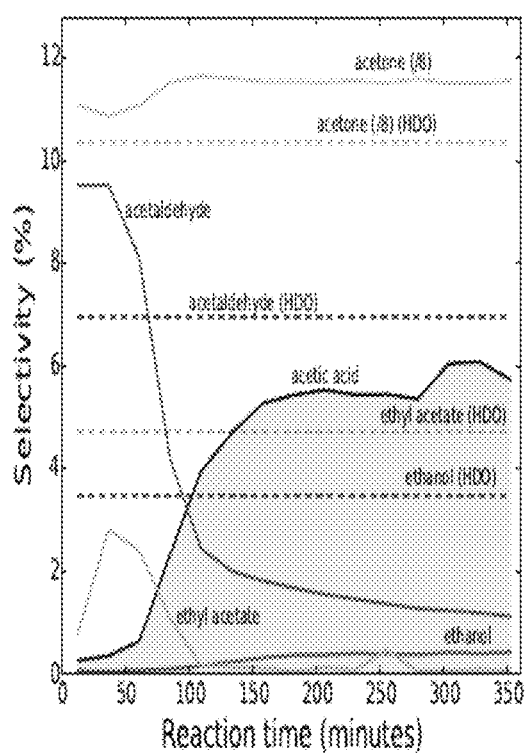
FIG. 12 is a graph of a looped-oxide catalysis (LOC) experiment which plots carbon-weighted selectivity as a function of reaction time for acetic acid and the dominant organic products of looped-oxide catalysis (LOC) with Zn catalyst.

Next, we used a reduced Zn catalyst in an argon environment with the same acetic acid reagent, in order to assess the LOC reaction (in a H2-free environment). Referring to FIG. 12, shows an LOC experiment which plots the carbon-weighted selectivity as a function of reaction time for acetic acid and the dominant organic products of LOC with Zn catalyst. The acetone selectivity values have been divided by eight for ease of reading. In FIG. 12, the selectivity toward dominant products of the 350° C. LOC experiment is plotted as a function of total reaction time, where the dotted lines give the corresponding product selectivity observed in the HDO experiment at 350° C. This reaction can be decomposed into two general temporal regimes. In the first regime, which lasts for the first sixty minutes of the reaction, the conversion of acetic acid to products is nearly complete. The selectivity to acetaldehyde is observed to be 9.5%, slightly higher than in the corresponding HDO experiment at 350° C., and a small amount of ethyl acetate formation is also observed. In the second regime, which spans the remainder of the reaction, selectivity towards acetaldehyde undergoes decay, accompanied by an increase in unreacted acetic acid. This trend likely corresponds to a diffusion-limited regime, in which a passivating zinc oxide layer has formed on the surface of the zinc particles, such that any coordinatively unsaturated surface sites at which acetic acid deoxygenation may occur necessarily derive from diffusion of oxygen vacancies through this oxide layer towards the surface.

In the selection and design of more effective LOC materials, one of the primary goals will be to extend the first regime of high selectivity towards deoxygenation. This might be accomplished by utilizing materials with faster diffusion characteristics as well as using nano-sized catalyst particles. As discussed earlier, zinc is known to form a passivating oxide layer with relatively slow diffusion kinetics as observed during the water-splitting step of solar thermochemical hydrogen production. Another objective in the design of LOC materials will be to achieve high selectivity towards deoxygenation without unwanted side reactions like the ketonization reaction of acetic acid to form acetone, as is known to occur on ZnO. It is worth noting that this was the dominant side reaction in both the LOC results and the HDO experiments.

The LOC results can help us to understand the results of the HDO reaction. First, as discussed in more detail in the next section, the similar selectivities of LOC to HDO, when LOC only has oxygen vacancies as a reductive source, suggests that a Mars-van Krevelen-type reaction is responsible for deoxygenation in both cases. Second, the observation that a decrease in ethyl acetate formation after 100 minutes coincides with decreased acetaldehyde formation supports the hypothesis that ethyl acetate is formed via the Tishchenko reaction:

$$2CH_3CHO \rightarrow CH_3COOCH_2CH_3 \quad (9)$$

Finally, it is important to note that a key objective of HDO catalysis is to achieve activity towards deoxygenation without expending $H_2$ on hydrogenation reactions that have relatively small energetic payoff (e.g. saturation of aromatic rings). By design, LOC achieves deoxygenation without hydrogenation by using a zero-valent metal or low-valence metal oxide as the reducing agent rather than $H_2$. This is demonstrated in FIG. 12, where it can be seen that LOC achieves selectivity towards the deoxygenation product, acetaldehyde, while selectivity towards the hydrogenation product, ethanol, is suppressed, since $H_2$ is not available for the hydrogenation.

In the upgrading scheme discussed herein, the reduced metal oxide acts as a well of reduction potential, which is drawn upon by reactions with bio-oil oxygenates occurring at the surface until the reduced metal oxide is completely re-oxidized and its reduction potential is exhausted. Experimentally, the direct deoxygenation of acetic acid to acetaldehyde during reaction with zinc metal demonstrated comparable selectivities with the analogous HDO of acetic acid over a zinc oxide catalyst. Based upon information and belief, HDO of oxygenate species on metal-oxide catalysts or oxide-supported transition metal catalysts generally occurs by a Mars-van Krevelen mechanism, in which the creation and destruction of surface oxygen vacancies are responsible for oxygen removal from the adsorbed species. A comparison of the experimental results of Zn/ZnO-catalyzed LOC and HDO gives strong support for the growing consensus that metal-oxide catalyzed HDO occurs via a Mars-van Krevelen mechanism, in which the active sites of the reaction are coordinatively-unsaturated metal surface sites (i.e. oxygen vacancies). The results demonstrate that zero-valent zinc metal is capable of direct deoxygenation of acetic acid to acetaldehyde in the absence of H2 and, furthermore, that the activity of this reaction decays as it progresses and the zinc metal surface is oxidized.

Figure 13:
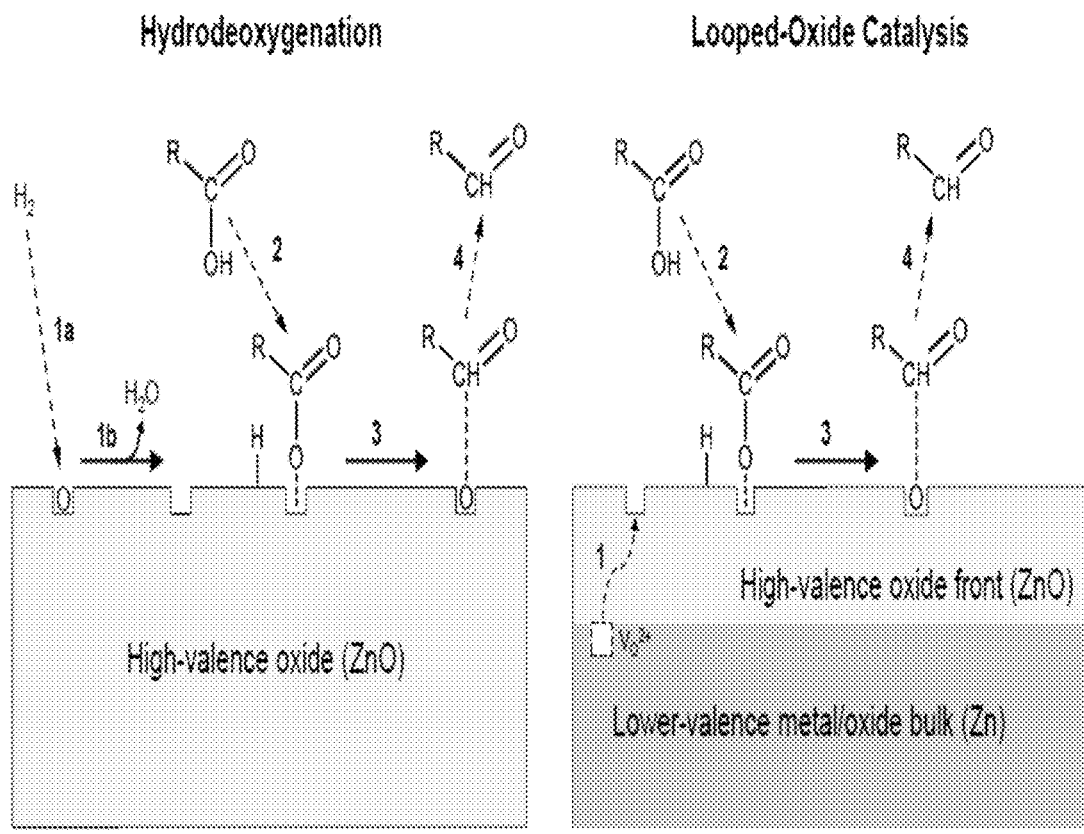
FIG. 13 is a schematic view of a generalized mechanism of carboxylic acid deoxygenation in looped-oxide catalysis (LOC), compared with the Mars-van Krevelen mechanism for hydrodeoxygenation (HDO).

A commonly proposed mechanism of HDO over metal oxide catalysts is essentially the reverse of that in selective oxidation, for which an extensive body of literature exists. Referring to FIG. 13, a schematic view is provided of a generalized mechanism of carboxylic acid deoxygenation in looped-oxide catalysis, compared with the Mars-van Krevelen mechanism for hydrodeoxygenation. The mechanism of metal-oxide catalyzed HDO of a carboxylic acid is illustrated on the left-hand side of FIG. 13. In step (1), the reaction of one molecule of H2 with a lattice oxygen atom in the oxide catalyst (i.e., zinc oxide) produces a molecule of water and leaves behind a single oxygen vacancy. The carboxylic acid species subsequently adsorbs onto the surface, filling in the vacancy with its own hydroxyl oxygen atom (2). This is followed by the transfer of a metal oxide surface hydroxyl hydrogen atom onto the central carbon atom (3), effectively forming an adsorbed aldehyde. In the final step (4), the aldehyde desorbs, leaving the surface restored to its original state.

Based on the experimental selectivity results discussed earlier, it is likely that the LOC upgrading reaction of a carboxylic acid with a zero-valent metal (e.g., zinc metal) or low-valence metal oxide occurs through a similar mechanism. The crucial distinction would be the source of oxygen vacancies: whereas oxygen vacancies in the HDO mechanism derive from the reaction of a lattice oxygen atom with gas phase $H_2$, in the LOC mechanism oxygen vacancies could diffuse from the reduced bulk of the catalyst particle through the formed high-valence oxide front (e.g., zinc oxide) to the surface where they would play the same role. The precise diffusion mechanism responsible for oxidation will depend on the structure of the metal oxide considered. While the zero-valent metal or low-valence metal oxide catalyst in its initial reduced state has no higher-valence oxide front (i.e., the entire surface is in a coordinatively unsaturated state), such a front would quickly develop and gradually increase in thickness as the reaction proceeds. This suggested LOC mechanism is illustrated in the right-hand side of FIG. 13. In step (1), a vacancy diffuses from the bulk to form a surface vacancy; steps (2)-(4) are identical to those in the HDO case.

In summary, the present invention provides a novel bio-oil upgrading pathway, looped-oxide catalysis (LOC), which harnesses solar thermal energy to drive bio-oil deoxygenation through the thermochemical cycling of a metal oxide; this metal oxide serves the dual function of catalytic surface and bulk reducing agent. Experimental results indicate that zero-valent zinc metal exhibits deoxygenation with selectivity comparable with that of hydrodeoxygenation (HDO) on zinc oxide. In addition to demonstrating the possibility of LOC upgrading, the selectivity results also suggest that both LOC and HDO operate via a vacancy-assisted Mars-van Krevelen mechanism in the Zn/ZnO system. LOC draws from the conceptual and technological framework of two existing processes; catalytic hydroprocessing and solar thermochemical water splitting, and as such stands to benefit from the ongoing research in each of these fields. LOC has several advantages over catalytic HDO of bio-oils that makes LOC a strong candidate as a complementary or alternate process:

1. Hydroprocessing (HDO) catalysts are designed with the goal of achieving selectivity towards deoxygenation without unnecessary hydrogenation. LOC achieves this goal by removing $H_2$ from the process altogether, enabling deoxygenation while suppressing hydrogenation.

2. The efficiency of HDO is restricted by the generation and compression of H2, while LOC is limited only by the solar thermal reduction of a metal oxide. Consequently, LOC exhibits best-case exergy efficiencies of 25 to 43%, while HDO with solar photovoltaic-generated hydrogen is limited by a best-case efficiency of around 30%.

3. HDO is typically operated at high pressures (100-200 bar) and a high partial pressure of H2, well in excess of the stoichiometrically specified amount. The LOC scheme may achieve the availability of oxygen vacancy sites on the metal oxide surface without requiring a high partial pressure of $H_2$, because these vacancies diffuse from within the reduced bulk of the oxide material itself.

4. An additional benefit of LOC is that the catalyst is renewed upon each iteration of the LOC cycle, avoiding the significant problem of long-term catalyst coking, which is prevalent in HDO processes.

Augmented biomass-to-fuels pathways such as LOC, which incorporate externally-generated renewable energy into the final fuel product, have the potential to enable up to a threefold increase in fuel yield over standalone processes for a given quantity of biomass. Such a dramatic change will be necessary to achieve complete replacement of petroleum-derived fuels in the United States and other regions where hydrocarbon fuel consumption exceeds the local biomass production capacity. There are many more metal oxide redox cycles with acceptable bulk thermodynamics than the five candidates identified in this perspective, especially when more complex materials than the binary metal oxides are considered. A thorough understanding of the characteristics of bio-oil deoxygenation upon reaction with zero-valent metals and low-valence metal oxides will allow for greater precision in achieving LOC deoxygenation and, in turn, can inform the design of better HDO catalysts by elucidating the role of surface oxygen vacancies in facilitating oxygen removal from adsorbed species.

In one embodiment, the deoxygenating is conducted at a pressure of 1-50 bar, preferably at a pressure of 1-10 bar, and more preferably at ambient total pressure.

In one embodiment, a hydrodeoxygenation process is conducted using $H_2$ generated through the in situ reaction of the low-valence or zero-valent metal oxide with water inside a reactor.

In one embodiment, the feedstock is a low-energy bioliquid. In another embodiment, the feedstock is bio-oil derived from thermal processing of lignocellulosic biomass.

In one embodiment, the zero-valent metal, the low-valence metal oxide, or the high-valence metal oxide comprises a metal that is selected from the group consisting of: Fe, Zn, Ge, Mo, Cd, Sn, Ce, W, or mixtures, combinations, or variations thereof. In another embodiment, the low-valence metal oxide or zero-valent metal is selected from the group consisting of: FeO, Zn, Cd, SnO, $Ce_2O_3$, or mixtures, combinations, or variations thereof. In another embodiment, the high-valence metal oxide is selected from the group consisting of: $Fe_3O_4$, ZnO, CdO, $SnO_2$, $CeO_2$ or mixtures, combinations, or variations thereof. Of course, it is contemplated that other low-valence metal oxides, zero-valent metals, or high-valence metal oxides may be used in accordance with parameters discussed herein.

In one embodiment, the zero-valent metal, said low-valence metal oxide, or said high-valence metal oxide acts as a catalyst in determining selectivity towards targeted deoxygenation products. In one embodiment, the zero-valent metal or said low-valence metal oxide acts as a bulk reducing agent and oxygen conductor in removing oxygen heteroatoms from the feedstock.

In one embodiment, the regenerating the low-valence metal oxide is performed within a solar thermal reactor.

In one embodiment, the deoxygenating of the feedstock occurs at a temperature between 300-700 K, preferably to a temperature between 400-600 K, and more preferably to a temperature of 500 K. Of course, these temperatures are preferred ranges which maybe subject to change depending upon the requirements of the reaction.

In one embodiment, the regenerating of the low-valence metal oxide occurs at a dissociation temperature of the high-valence metal oxide.

In one embodiment, the regenerating of the low-valence metal oxide occurs at temperature between 1000-2000 K, preferably to a temperature between 1200-1800 K, more preferably to a temperature between 1400-1600, and even more preferably at 1500 K. Of course, these temperatures are preferred ranges which maybe subject to change depending upon the requirements of the reaction.

In one embodiment, regenerating a low-valence metal oxide is accomplished in a solar electrothermal reactor where the metal oxide is dissolved in a molten electrolyte.

Therefore, while there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. An integrated thermochemical process for providing an upgraded biofuel composition from a biomass-derived feedstock, comprising:
   deoxygenating the feedstock through reaction with a low-valence metal oxide or zero-valent metal to yield a deoxygenated biofuel composition and a high-valence metal oxide; and
   reducing the high-valence metal oxide using solar thermal energy, thereby regenerating the low-valence metal oxide.

2. The process of claim 1, wherein the deoxygenating is conducted at a pressure of 1-50 bar.

3. The process of claim 1, wherein:
   deoxygenating the feedstock is accomplished through a hydrodeoxygenation process; and
   the hydrodeoxygenation process is conducted using $H_2$ generated through an in situ reaction of the low-valence or zero-valent metal oxide with water inside a reactor.

4. The process of claim 1, wherein the feedstock is a bioliquid.

5. The process of claim 1, wherein the feedstock is bio-oil derived from thermal processing of lignocellulosic biomass.

6. The process of claim 1, wherein said zero-valent metal, said low-valence metal oxide, or said high-valence metal oxide comprises a metal that is selected from the group consisting of: Fe, Zn, Ge, Mo, Cd, Sn, Ce, and W.

7. The process of claim 1, wherein said zero-valent metal, said low-valence metal oxide, or said high-valence metal oxide acts as a catalyst in determining selectivity towards targeted deoxygenation products.

8. The process of claim 1, wherein said zero-valent metal or said low-valence metal oxide acts as a bulk reducing agent and oxygen conductor in removing oxygen heteroatoms from the feedstock.

9. The process of claim 1, wherein reducing the high-valence metal oxide is performed within a solar thermal reactor.

10. The process of claim 1, wherein the deoxygenating of the feedstock occurs at a temperature between 300-700 K.

11. The process of claim 1, wherein the regenerating of the low-valence metal oxide occurs at a dissociation temperature of the high-valence metal oxide.

12. The process of claim 11, wherein the regenerating of said low-valence metal oxide occurs at a temperature between 1000-2000 K.

13. The process of claim 1, wherein the low-valence metal oxide or zero-valent metal is selected from the group consisting of: FeO, Zn, Cd, SnO and $Ce_2O_3$.

14. The process of claim 1, wherein the high-valence metal oxide is selected from the group consisting of: $Fe_3O_4$, ZnO, CdO, $SnO_2$, and $CeO_2$.

15. The process of claim 1, wherein regenerating a low-valence metal oxide is accomplished in a solar electrothermal reactor where the metal oxide is dissolved in a molten electrolyte.

16. The process of claim 1, wherein the deoxygenating is conducted at a pressure of 1-10 bar.

17. The process of claim 1, wherein the deoxygenating is conducted at ambient total pressure.

18. The process of claim 1, wherein the deoxygenating of the feedstock occurs at a temperature between 400-600 K.

19. The process of claim 11, wherein the regenerating of said low-valence metal oxide occurs at a temperature between 1400-1600 K.

20. The process of claim 11, wherein the regenerating of said low-valence metal oxide occurs at a temperature of 1500 K.

* * * * *